US012690978B2

(12) United States Patent
Sperling

(10) Patent No.: US 12,690,978 B2
(45) Date of Patent: Jul. 28, 2026

(54) SYSTEM FOR CUSTOM IMPLANT DESIGN AND INSTRUMENTATION

(71) Applicant: MAYO FOUNDATION FOR MEDICAL EDUCATION AND RESEARCH, Rochester, MN (US)

(72) Inventor: John W. Sperling, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 19/399,229

(22) Filed: Nov. 24, 2025

(65) Prior Publication Data

US 2026/0083568 A1      Mar. 26, 2026

Related U.S. Application Data

(63) Continuation of application No. PCT/US2025/023638, filed on Apr. 8, 2025.
(Continued)

(51) Int. Cl.
*A61F 2/40* (2006.01)
*A61B 17/16* (2006.01)
(Continued)

(52) U.S. Cl.
CPC ........ *A61F 2/4081* (2013.01); *A61B 17/1637* (2013.01); *A61B 17/1778* (2016.11); *A61F 2/30942* (2013.01); *A61F 2/4612* (2013.01); *A61B 17/1684* (2013.01); *A61B 2017/568* (2013.01); *A61F 2002/4687* (2013.01)

(58) Field of Classification Search
CPC ............ A61B 17/1778; A61B 17/1684; A61B 2017/568; A61F 2002/4687; A61F 2/4612
See application file for complete search history.

(56) References Cited

U.S. PATENT DOCUMENTS 9,393,032 B2    7/2016  Carignan et al.
9,492,182 B2   11/2016  Keefer
(Continued)

OTHER PUBLICATIONS

International Search Report and Written Opinion for International Application No. PCT/US2025/023638 dated Jul. 14, 2025, 23 pages.

*Primary Examiner* — Javier G Blanco
(74) *Attorney, Agent, or Firm* — Meunier Carlin & Curfman LLC

(57) ABSTRACT

Systems and methods include a component of a bone implant that includes a patient specific bone contacting surface and, optionally, at least one protrusion adjacent to or extending from the patient specific bone contacting surface. The at least one protrusion is configured for engaging a bone preparation in the bone. To prepare the bone for receiving the component, one or more cutting tool templates may be used. The one or more cutting tool templates may be fabricated to have a patient specific bone contacting surface that engages the bone that is to receive the implant component. A cutting tool is engaged in one or more of one or more slots defined by the cutting tool template(s) to remove surface portions of the bone to create the bone preparation for engaging the protrusion. The patient specific bone contacting surface of the component engages the bone.

9 Claims, 36 Drawing Sheets

Related U.S. Application Data

(60) Provisional application No. 63/631,086, filed on Apr. 8, 2024.

(51) Int. Cl.

| | | |
|---|---|---|
| *A61B 17/17* | (2006.01) | |
| *A61F 2/30* | (2006.01) | |
| *A61F 2/46* | (2006.01) | |
| *A61B 17/56* | (2006.01) | |

(56) References Cited

U.S. PATENT DOCUMENTS

| | | | |
|---|---|---|---|
| 10,849,636 B2 | 12/2020 | Hafez | |
| 11,234,719 B2 | 2/2022 | Vanasse et al. | |
| 2004/0153163 A1* | 8/2004 | Posner | A61B 17/155 |
| | | | 623/20.14 |
| 2011/0071533 A1* | 3/2011 | Metzger | A61B 17/155 |
| | | | 606/88 |
| 2012/0290272 A1* | 11/2012 | Bryan | A61B 17/1684 |
| | | | 703/1 |
| 2013/0110116 A1* | 5/2013 | Kehres | A61B 17/1739 |
| | | | 606/96 |
| 2013/0150975 A1* | 6/2013 | Iannotti | A61F 2/4059 |
| | | | 623/19.11 |
| 2017/0000503 A1* | 1/2017 | Keefer | A61B 17/1615 |
| 2019/0069913 A1* | 3/2019 | Iannotti | A61B 17/151 |
| 2021/0220151 A1* | 7/2021 | Deransart | A61F 2/4612 |
| 2022/0183703 A1* | 6/2022 | Chi | A61B 17/1742 |
| 2023/0310097 A1 | 10/2023 | Chi | |

* cited by examiner

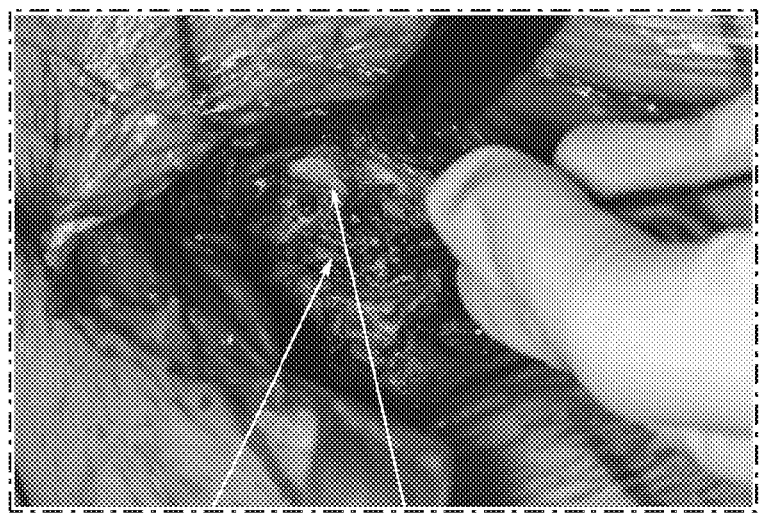
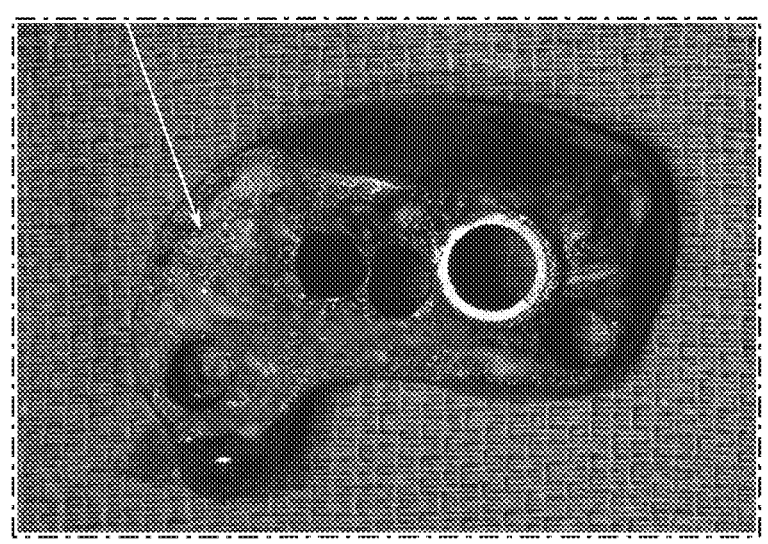
FIG. 1B
PRIOR ART

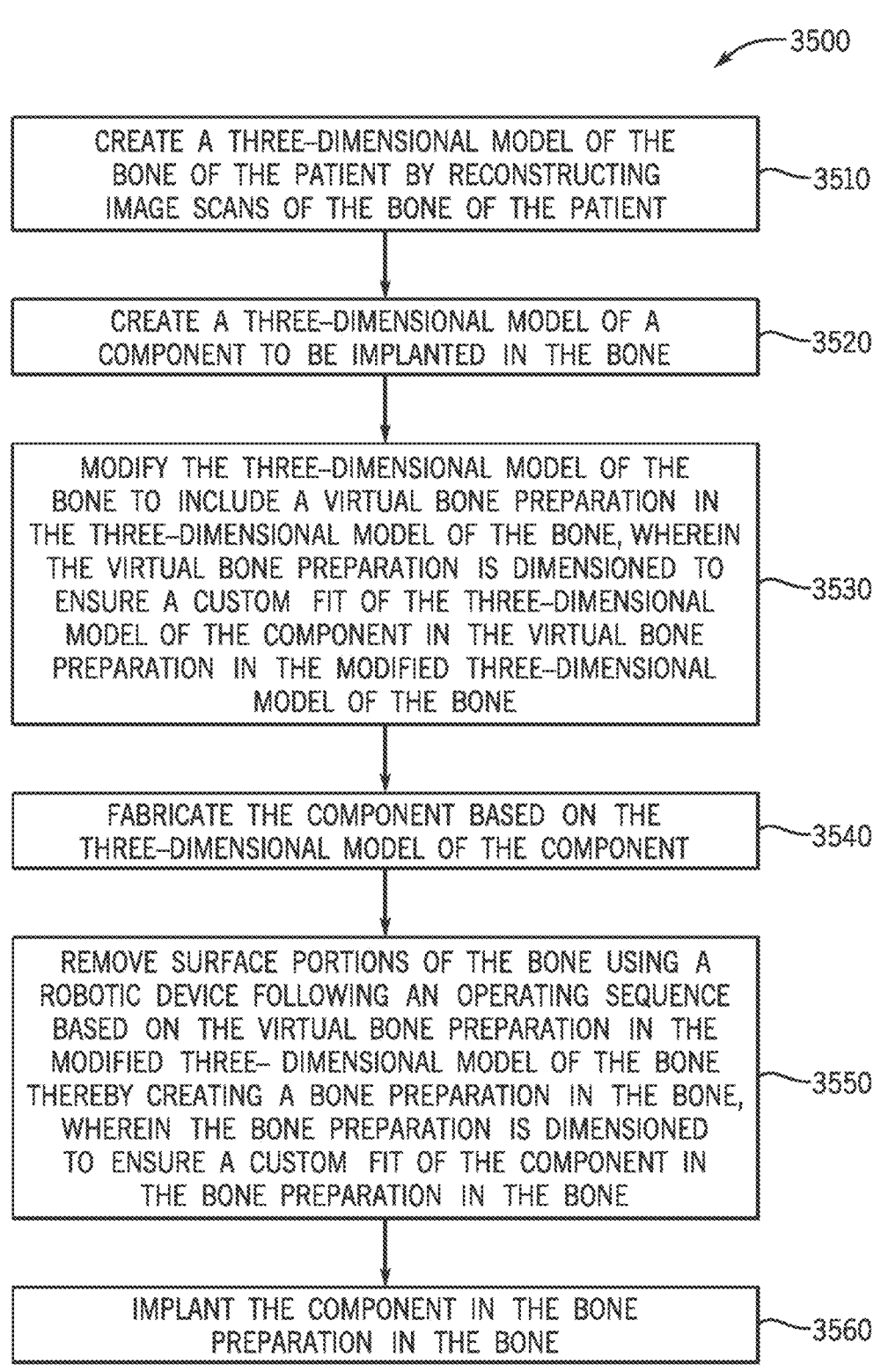

—3500

CREATE A THREE-DIMENSIONAL MODEL OF THE
BONE OF THE PATIENT BY RECONSTRUCTING
IMAGE SCANS OF THE BONE OF THE PATIENT
—3510

CREATE A THREE-DIMENSIONAL MODEL OF A
COMPONENT TO BE IMPLANTED IN THE BONE
—3520

MODIFY THE THREE-DIMENSIONAL MODEL OF THE
BONE TO INCLUDE A VIRTUAL BONE PREPARATION IN
THE THREE-DIMENSIONAL MODEL OF THE BONE, WHEREIN
THE VIRTUAL BONE PREPARATION IS DIMENSIONED TO
ENSURE A CUSTOM FIT OF THE THREE-DIMENSIONAL
MODEL OF THE COMPONENT IN THE VIRTUAL BONE
PREPARATION IN THE MODIFIED THREE-DIMENSIONAL
MODEL OF THE BONE
—3530

FABRICATE THE COMPONENT BASED ON THE
THREE-DIMENSIONAL MODEL OF THE COMPONENT
—3540

REMOVE SURFACE PORTIONS OF THE BONE USING A
ROBOTIC DEVICE FOLLOWING AN OPERATING SEQUENCE
BASED ON THE VIRTUAL BONE PREPARATION IN THE
MODIFIED THREE- DIMENSIONAL MODEL OF THE BONE
THEREBY CREATING A BONE PREPARATION IN THE BONE,
WHEREIN THE BONE PREPARATION IS DIMENSIONED
TO ENSURE A CUSTOM FIT OF THE COMPONENT IN
THE BONE PREPARATION IN THE BONE
—3550

IMPLANT THE COMPONENT IN THE BONE
PREPARATION IN THE BONE
—3560

FIG. 35

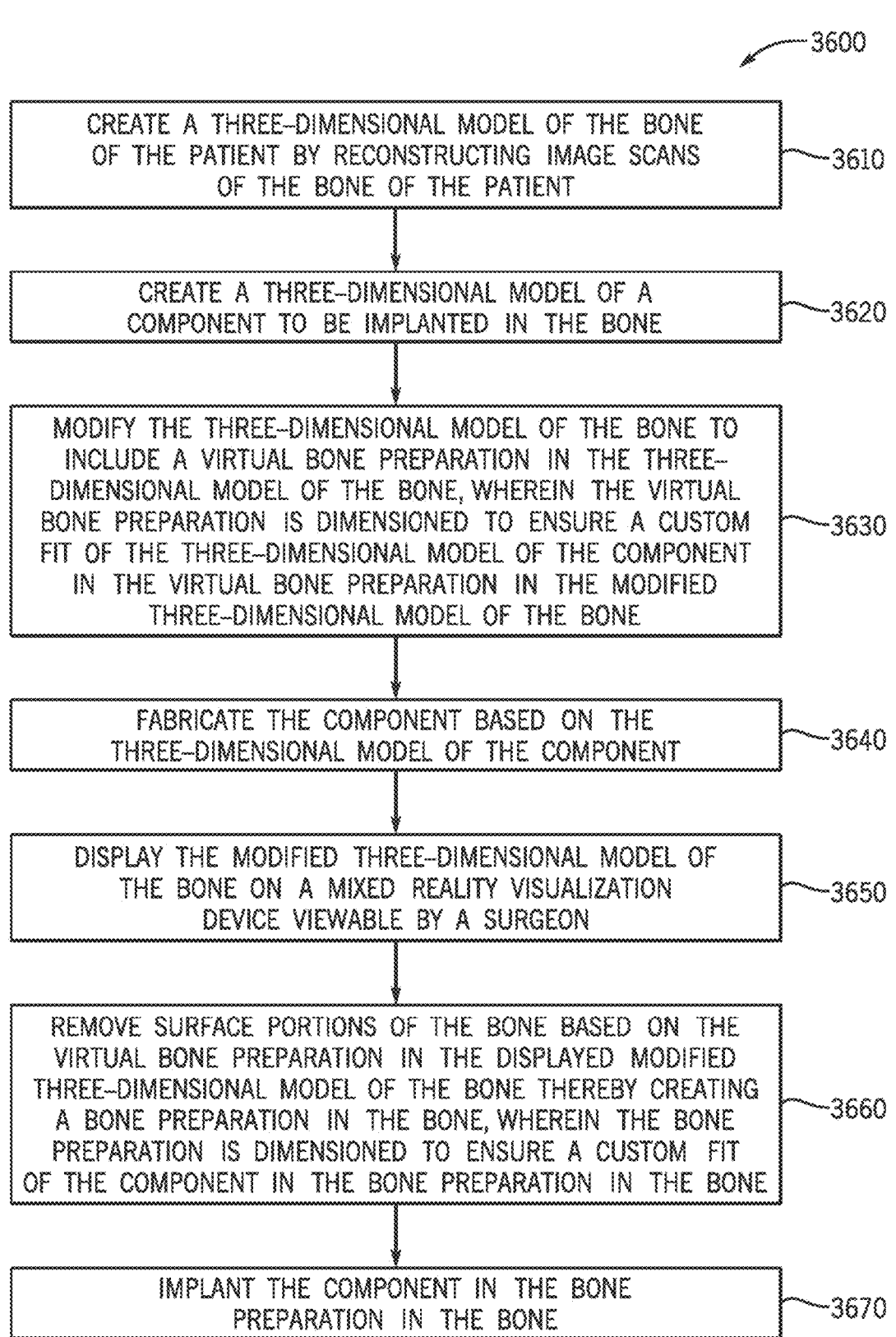

~3600

CREATE A THREE-DIMENSIONAL MODEL OF THE BONE
OF THE PATIENT BY RECONSTRUCTING IMAGE SCANS
OF THE BONE OF THE PATIENT
~3610

CREATE A THREE-DIMENSIONAL MODEL OF A
COMPONENT TO BE IMPLANTED IN THE BONE
~3620

MODIFY THE THREE-DIMENSIONAL MODEL OF THE BONE TO
INCLUDE A VIRTUAL BONE PREPARATION IN THE THREE-
DIMENSIONAL MODEL OF THE BONE, WHEREIN THE VIRTUAL
BONE PREPARATION IS DIMENSIONED TO ENSURE A CUSTOM
FIT OF THE THREE-DIMENSIONAL MODEL OF THE COMPONENT
IN THE VIRTUAL BONE PREPARATION IN THE MODIFIED
THREE-DIMENSIONAL MODEL OF THE BONE
~3630

FABRICATE THE COMPONENT BASED ON THE
THREE-DIMENSIONAL MODEL OF THE COMPONENT
~3640

DISPLAY THE MODIFIED THREE-DIMENSIONAL MODEL OF
THE BONE ON A MIXED REALITY VISUALIZATION
DEVICE VIEWABLE BY A SURGEON
~3650

REMOVE SURFACE PORTIONS OF THE BONE BASED ON THE
VIRTUAL BONE PREPARATION IN THE DISPLAYED MODIFIED
THREE-DIMENSIONAL MODEL OF THE BONE THEREBY CREATING
A BONE PREPARATION IN THE BONE, WHEREIN THE BONE
PREPARATION IS DIMENSIONED TO ENSURE A CUSTOM FIT
OF THE COMPONENT IN THE BONE PREPARATION IN THE BONE
~3660

IMPLANT THE COMPONENT IN THE BONE
PREPARATION IN THE BONE
~3670

SYSTEM FOR CUSTOM IMPLANT DESIGN AND INSTRUMENTATION

CROSS-REFERENCE TO RELATED APPLICATIONS

This application is a continuation application of PCT/US25/23638 filed Apr. 8, 2025, which claims the benefit of priority to U.S. Provisional Application No. 63/631,086 filed Apr. 8, 2024, which is hereby incorporated herein by reference in its entirety.

STATEMENT REGARDING FEDERALLY SPONSORED RESEARCH

Not Applicable.

BACKGROUND

1. Field of the Invention

The disclosure relates to a system for custom medical implant design and instrumentation.

2. Description of the Related Art

Various prostheses for the replacement of the shoulder joint are known. In one example shoulder prosthesis, the upper portion of the humerus is replaced by a humeral component including (i) a stem that extends into a bore formed within the humerus and (ii) a generally hemispherical head portion that is connected to the stem. The hemispherical head of the humeral component articulates with a complementary concave section of a glenoid component mounted within the glenoid cavity of the scapula. This type of shoulder prosthesis may be called a "primary" or "total" prosthesis. In another example shoulder prosthesis, often called a "reverse" or "inverted" prosthesis, the glenoid component includes a convex section that articulates with a complementary concave section of the head of the humeral component.

One alternative to total shoulder replacement is referred to as shoulder hemiarthroplasty. The humeral head is replaced with a generally hemispherical head that may or may not include a connected stem. The glenoid cavity of the scapula is not replaced with a glenoid component, but may be refinished in a way that gives it a smooth surface and a shape which matches the generally hemispherical replacement head.

Several deficiencies have been found in currently available shoulder arthroplasty systems including glenoid sizes (primary and reverse) and humeral sizes that are not based on the anatomic distribution. Patient specific technology has begun to be applied to shoulder arthroplasty to address the problems associated with standard off the shelf components that are not based on anatomic sizes. Such patient specific technology can involve obtaining medical images of the shoulder joint of a patient, and from that imaging, custom implant components can be designed to match the bony anatomy of the specific patient. However, compared to off the shelf implants, inherent challenges with custom implant components can result in implant failure.

One drawback with custom implant components is that there is no instrumentation available to prepare the bone surface. In non-custom implant cases, surgeons are supplied precise instrumentation to create a bleeding bony surface conducive to bone ingrowth. The instrumentation removes any fibrous tissue which can prevent bone ingrowth and allows full seating of the implant on the bone. The instrumentation plays a critical role in stimulating the bone surface to present a bleeding bony surface that optimizes bone ingrowth into the porous surface of the custom component. The instrumentation also results in a clearly defined area of bone preparation that ensures accurate placement of an implant and aids in time zero stability with compression. Companies that manufacture custom implants do not currently provide surgeons with any tools to address the critical step of bone preparation. Due to the inherent asymmetric shape of custom components, there is not an available means to remove a uniform amount of bone from an asymmetric bone surface to create a bleeding bone surface. Many patients have varying amounts of cartilage or soft tissue present that prevents the custom implant from sitting directly on the bone surface. Moreover, the bone that is frequently present can be extremely sclerotic with minimal blood flow making bone ingrowth into the implant challenging.

Another drawback with custom implant components is that there is no instrumentation to create a clearly defined area of bone preparation. In non-custom implant cases, the instrumentation creates a very clearly defined area to assist the surgeon in placing the implant in the correct position. This helps ensure accurate placement of an implant and aids in time zero implant stability. There is no instrumentation for custom implants to create this clearly defined area. This results in the surgeon making a guess at the implant position.

Another drawback with custom implant components is that there is no instrumentation to precisely place the custom implant. In non-custom implant cases, instrumentation is available to allow the accurate placement of the implant on the bone surface in all three planes ensuring direct contact between the implant and bone. Direct contact is essential to ensure that bone grows into the implant for long term stability. An inserter is used for the implant to place it precisely. When performing a custom implant, it is very difficult to determine whether the implant is sitting correctly in the bone in all three planes. The operative space is very tight and since the implant does not sit within the boundaries of a prepared bone surface, the rotation of the implant can be incorrect without the surgeon recognizing the malposition. Without instrumentation, the surgeon is essentially guessing whether the implant is in the correct location. Research has shown that just 5 degrees of malrotation of a symmetric implant can decrease contact by more than 50%. This is likely worse with a custom implant due to the irregularly shaped surfaces. One can see radiographic examples of custom implants where there is a halo around the implant indicating that the implant is not in close apposition to the bony surface. There is abundant research that an implant must be directly opposed to a bone surface without a gap to allow for bone ingrowth with less than a 50 micron gap. The 1000 micron (1 millimeter) gaps that are frequently present with custom implants significantly increase the chances of loosening and failure.

Another drawback with custom implant components is that custom implants do not have design features that facilitate placement and enhance stability. As noted above, currently there is no method to ensure the accurate preparation of the bone surface, optimize the biologic environment for bony ingrowth, and ensure accurate placement.

Notwithstanding the drawbacks with custom implants, there continues to be dramatic interest in leveraging 3D printing to create custom orthopedic implants. From glenoid components in shoulder replacement to acetabular shells in hip replacement, custom implants can be designed with the goal to match the bony anatomy of a patient. Compared to off the shelf implants, it has been recognized as noted above that there are inherent challenges with custom components that can result in a high rate of failure. In summary, there are four key principles of successful orthopedic surgery that are routinely performed when implanting a standard off the shelf non-custom implant that are not available with custom implants leading to increased failure: (1) instrumentation that results in precise bone preparation to create an optimal bleeding bony environment for bone ingrowth into the implant for long term stability, (2) a clearly defined area of bone preparation that ensures accurate placement of an implant and aids in time zero implant stability, (3) simple and accurate means to ensure the implant is inserted in the correct orientation, and (4) implant specific design features that facilitates accurate placement and increase implant stability.

Therefore, there is a need for an improved system for custom medical implant design and instrumentation that addresses each of these key drawbacks of custom implants.

SUMMARY OF THE DISCLOSURE

The present disclosure provides an improved system for custom medical implant design and instrumentation that address each of these key drawbacks of custom implants. The applications of this technology include orthopedic as well as any application where custom implants are used to match a bone surface including but not limited to dental and maxillofacial applications. In various implementations, a custom component contains at least one built-in protrusion that accurately matches the prepared surface. In some implementations, the engagement of the protrusion with recesses on the prepared surface facilitates bone ingrowth, accurate placement, and enhanced stability (e.g., rotational stability). Therefore, various implementations disclosed herein provide systems for custom medical implant design and instrumentation that address the aforementioned problems. The systems disclosed herein are not limited to orthopedic surgery and are applicable to any procedure where a custom implant will be placed on a bone surface (orthopedic, dental, otolaryngology in humans or animals).

In one aspect, the present disclosure provides a locating device for use in implanting a component of an implant in a bone of a patient, wherein the locating device comprises a locating pin guide.

In another aspect, the present disclosure provides a system for preparation of a surface of a bone of a patient when implanting a component of an implant in the bone of the patient, wherein the system comprises a cutting tool template.

In another aspect, the present disclosure provides a system for implanting a component of an implant in the bone of the patient, wherein the component has a first surface and a bone contacting surface configured to contact the bone for ensuring a custom fit of the component and a predetermined surface region on the bone, wherein the system comprises an insertion instrument.

In another aspect, the present disclosure provides a kit for use in implanting a component of an implant in a bone of a patient.

In another aspect, the present disclosure provides a method for implanting a component of an implant in a bone of a patient.

In another aspect, the present disclosure provides another method for implanting a component of an implant in a bone of a patient.

In another aspect, the present disclosure provides yet another method for implanting a component of an implant in a bone of a patient.

Various implementations include a reproducible system to manufacture a custom orthopedic implant component(s) and associated instrumentation. The instrumentation facilitates preparation of the bone surface with removal of any fibrous tissue or cartilage which would hinder bone ingrowth. It allows for a repeatable depth of bone preparation, resulting in an optimized biologic environment for bone ingrowth. The patient specific implant component(s) is manufactured to have at least one distal protrusion having a length, measured proximally to distally, to match the depth of the bone preparation. The patient specific implant component(s) is manufactured to have a consistent porous surface which matches the shape of the bone preparation. The bone preparation may include one or more recesses and/or recessed surface contours. The engagement of the at least one protrusion with the bone preparation allows the custom implant component(s) to provide tactile immediate feedback to the surgeon that the custom implant component(s) is placed in the correct location with increased stability. The implant component(s) may have the identical shape and/or dimensions of the bone surface to which the implant is to be coupled. However, in some implementations, the implant component(s) or portions thereof may be slightly larger (e.g., greater than 0 and less than 2 mm larger) than the bone surface to provide for an interference fit between the bone surface and the implant component(s).

Multiple iterations of the custom instrumentation were developed to improve the accuracy and streamline the number of steps. The system of the present disclosure was verified for reproducible bone preparation using plastic models as well as in cadaveric specimens with arthritis.

It is one advantage of various implementations of the present disclosure to provide custom instrumentation that results in precise bone preparation to create an optimal bleeding bony environment for bone ingrowth into a custom implant for long term stability.

It is another advantage of various implementations of the present disclosure to provide custom instrumentation that results in a clearly defined area of bone preparation that ensures accurate placement of a custom implant and aids in time zero custom implant stability.

It is another advantage of various implementations of the present disclosure to provide simple and accurate means to ensure a custom implant is inserted in the correct orientation.

It is another advantage of various implementations of the present disclosure to provide custom implant specific design features that facilitate accurate placement and increase custom implant stability.

These and other features, aspects, and advantages of the present disclosure will become better understood upon consideration of the following detailed description, drawings, and appended claims.

BRIEF DESCRIPTION OF THE DRAWINGS

FIG. 1B shows photographs of a failed custom glenoid implant.

FIG. 35 is a flow chart of a method according to one example implementation of the present disclosure.

FIG. 36 is a flow chart of another method according to one example implementation of the present disclosure.

Like reference numerals will be used to refer to like parts from Figure to Figure in the following description of the drawings.

US 12,690,978 B2

7

DETAILED DESCRIPTION

Various implementations include systems that comprise one or more instruments and/or one or more components of an implant suitable for coupling to a bone of a patient. The one or more instruments may be suitable for preparing a bone surface of the bone of the patient and/or installing the one or more components of the implant to the bone surface of the patient.

Various implementations include methods for manufacturing one or more instruments and/or one or more components of an implant suitable for coupling to a bone of a patient. The one or more instruments may be suitable for preparing a bone surface of the bone of the patient and/or coupling the one or more components of the implant to the bone surface of the patient.

As used herein, "patient" is a mammal, preferably a human.

Figure 4A:
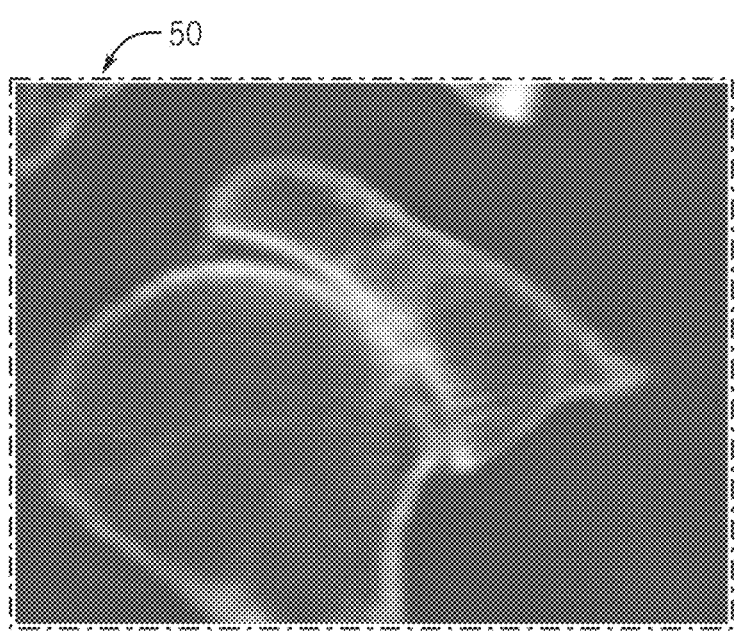
FIG. 4A shows a two-dimensional computer tomography slice of the scapula of a patient.
Figure 4B:
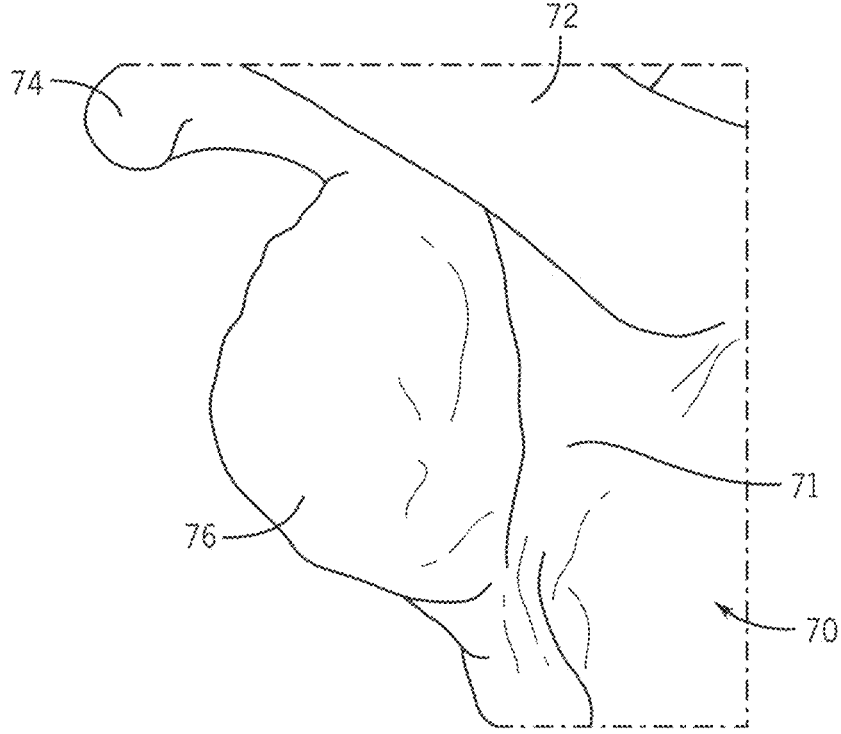
FIG. 4B shows a three-dimensional model of the scapula of the patient created from a stack of 2D slices similar to FIG. 4A.

In a first step of a method, according to some implementations, a three-dimensional model of the bone of the patient is created by reconstructing image scans of the bone of the patient. Digital patient-specific image information can be provided by any suitable means known in the art, such as a computer tomography (CT) scanner, a magnetic resonance imaging (MRI) scanner, or a combination thereof. For example, the step may comprise the steps of obtaining 2D datasets of the bone of the patient and reconstructing a 3D virtual bone model from the 2D datasets. The output of the bone scan can be a stack of two-dimensional (2D) slices forming a 3D data set. The output of the scan can be digitally imported into a computer program and may be converted using algorithms known in the field of medical image processing technology to produce a 3D computer model of the relevant bone of the patient. FIG. 4A shows an example two-dimensional (2D) CT slice 50 of the scapula of a patient, and FIG. 4B shows a three-dimensional model 70 of the scapula 71 of the patient created from a stack of 2D slices similar to FIG. 4A. The scapula 71 has an acromion 72, a coracoid process 74, and a glenoid cavity 76.

Figure 5:
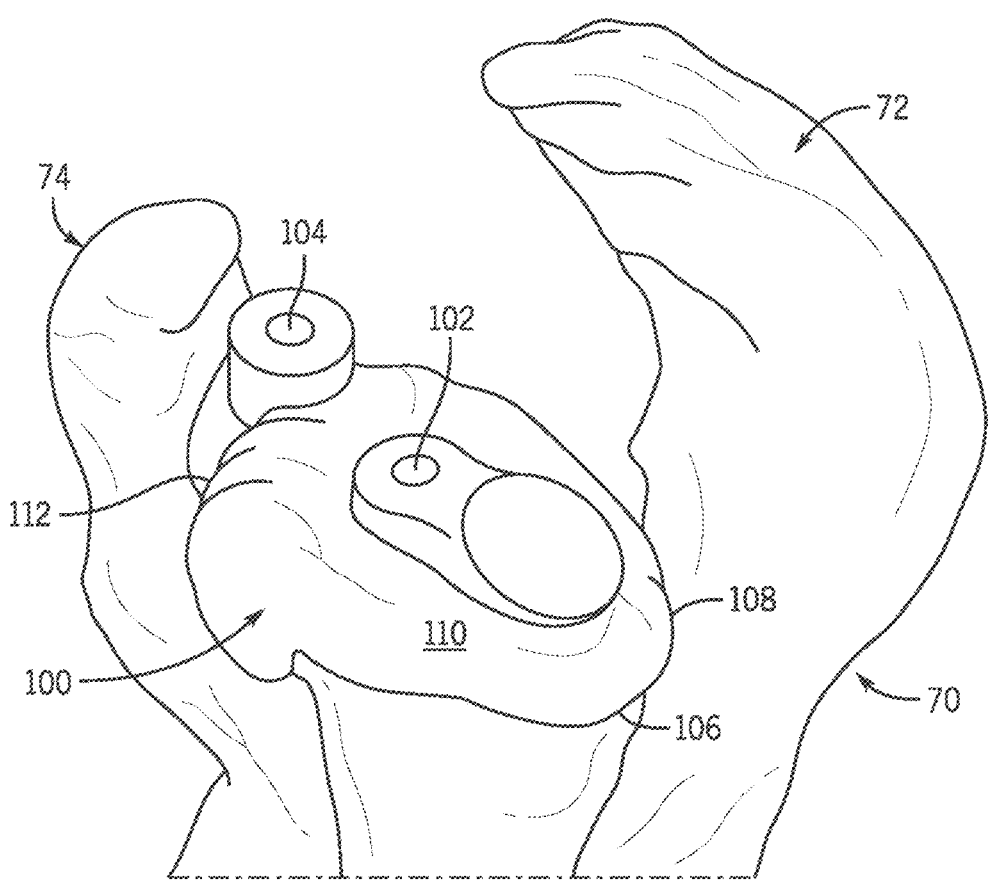
FIG. 5 is a perspective view of a locating pin guide according to one example implementation of the present disclosure positioned on a scapula.

In a second step of the method, a locating pin guide 100 is fabricated. Referring now to FIG. 5, the locating pin guide 100 has an inner throughhole 102, an outer throughhole 104, and a patient specific bone contacting surface 106 configured to contact the scapula 71 for ensuring a custom fit of the locating pin guide 100 and a predetermined surface region on the scapula 71. The custom fit of the locating pin guide 100 and the predetermined surface region on the scapula 71 extends from a first border 108 of the locating pin guide 100 across an inner region 110 of the locating pin guide 100 to a second border 112 of the locating pin guide 100. The locating pin guide 100 is dimensioned such that an inner surface of the outer throughhole 104 is spaced apart from the predetermined surface region on the scapula 71 when the patient specific bone contacting surface 106 matingly engages the predetermined surface region on the scapula 71. In one implementation, a longitudinal axis of the inner throughhole 102 is directed into an inner region of a glenoid cavity 76 of the scapula 71 when the patient specific bone contacting surface 106 matingly engages the predetermined surface region on the scapula 71. In one implementation, a longitudinal axis of the outer throughhole 104 is directed into a base of the coracoid 74 of the scapula 71 when the patient specific bone contacting surface 106 matingly engages the predetermined surface region on the scapula 71.

In one implementation, a glenoid pin 114 (see FIG. 23) is dimensioned for insertion through the inner throughhole 102 and into the glenoid cavity 76, and a coracoid pin 116 (see

8

Figure 23:
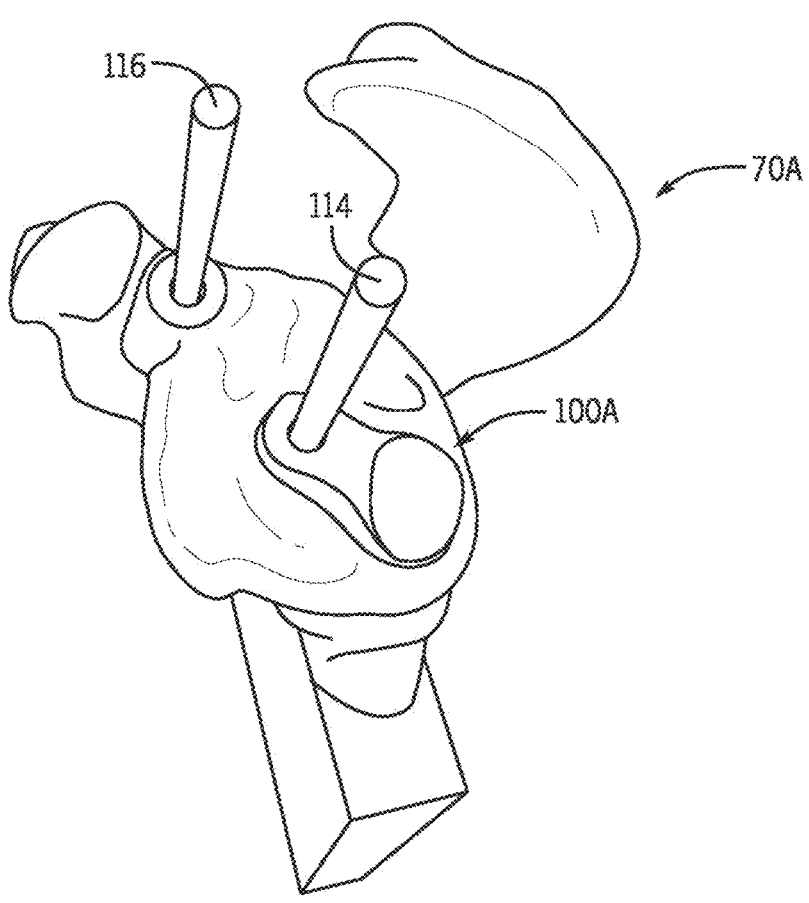
FIG. 23 is a perspective view of a locating pin guide according to one example implementation of the present disclosure positioned on a scapula model.

FIG. 23) is dimensioned for insertion through the outer throughhole 104 and into the coracoid 74. In one implementation, the coracoid pin 116 and the glenoid pin 114 are parallel when the glenoid pin 114 is inserted through the inner throughhole 102 and into the glenoid cavity 76 and the coracoid pin 116 is inserted through the outer throughhole 104 and into the coracoid 74. The glenoid pin 114 (or an alternative hole-forming instrument) is dimensioned for insertion through the inner throughhole 102 and into the glenoid cavity 76 to create a positioning hole 144 (see FIG. 24) in the glenoid cavity 76.

In one implementation, the patient specific bone contacting surface 106 has a complementary shape to a bone surface of the three-dimensional model 70 of the scapula 71 of the patient reconstructed from image scans of the scapula 71 of the patient. The locating pin guide 100 can be fabricated using 3D printing based on the three-dimensional model 70 of the scapula 71 of the patient.

Figures 6, 7, 8:
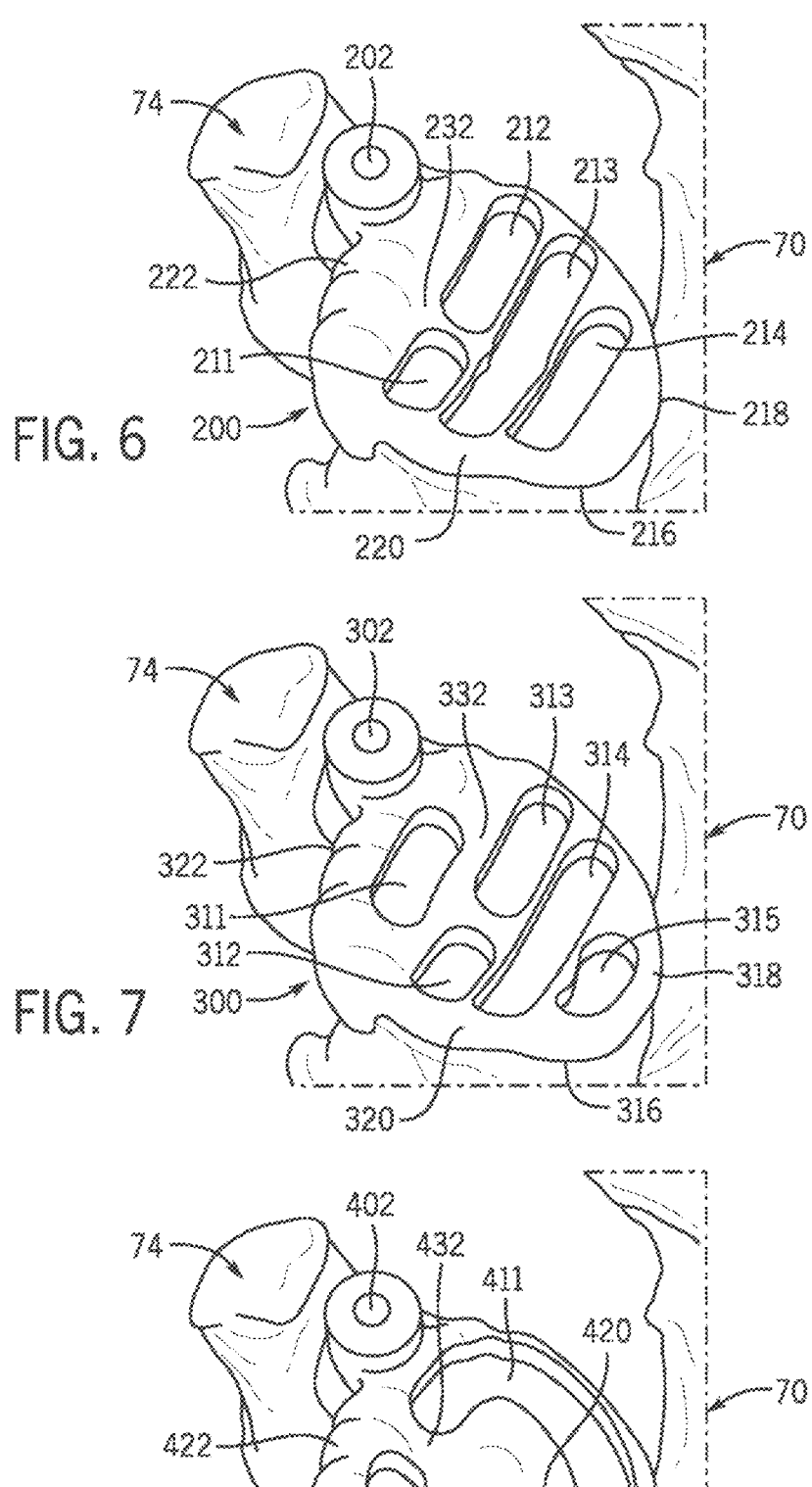
FIG. 6 is a perspective view of a first cutting tool template according to one example implementation of the present disclosure positioned on a scapula.
FIG. 7 is a perspective view of a second cutting tool template according to one example implementation of the present disclosure positioned on a scapula.
FIG. 8 is a perspective view of a third cutting tool template according to one example implementation of the present disclosure positioned on a scapula.
Figure 9:
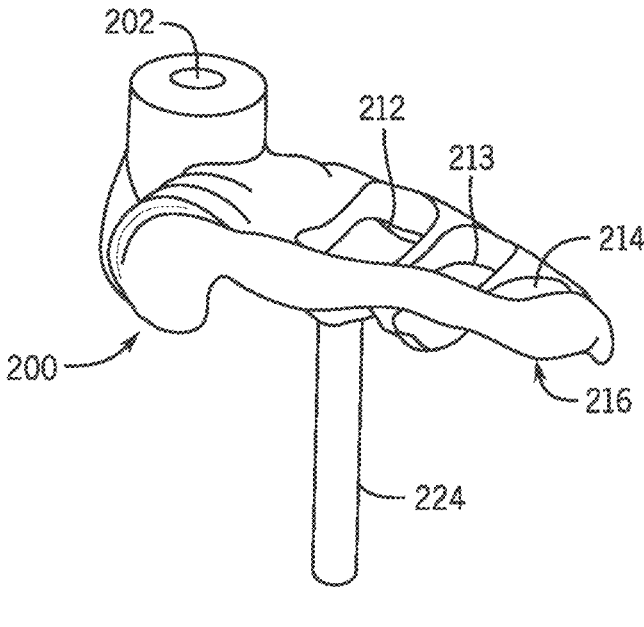
FIG. 9 is a side view of a first cutting tool template according to one example implementation of the present disclosure positioned on a scapula.
Figure 10:
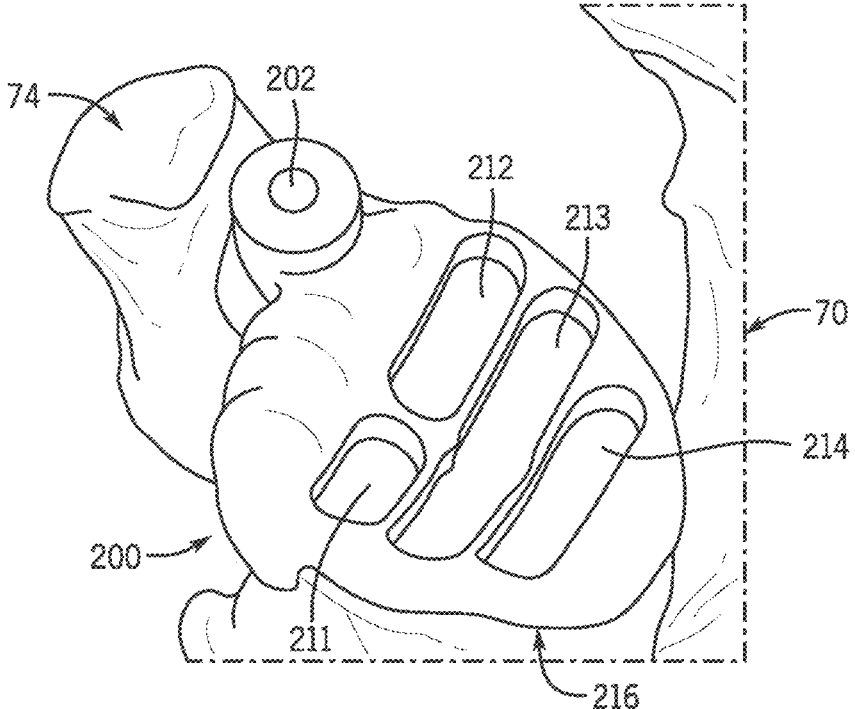
FIG. 10 is a perspective view of the first cutting tool template of FIG. 9 positioned on a scapula.

In a third step of the method, a first cutting tool template 200 is fabricated. Referring now to FIGS. 6, 9, and 10, the first cutting tool template 200 has a locating pin hole 202 dimensioned to receive the coracoid pin 116, a plurality of cutting guide slots 211, 212, 213, 214 dimensioned to receive a cutting tool, and a patient specific bone contacting surface 216. The patient specific bone contacting surface 216 is configured to contact the scapula 71 for ensuring a custom fit of the first cutting tool template 200 and a predetermined region on the scapula 71. The custom fit of the first cutting tool template 200 and the predetermined surface region on the scapula 71 extends from a first border 218 of the first cutting tool template 200 across an inner region 220 of the first cutting tool template 200 to a second border 222 of the first cutting tool template 200. The first cutting tool template 200 is dimensioned such that an inner surface of the locating pin hole 202 is spaced apart from the predetermined surface region on the scapula 71 when the patient specific bone contacting surface 216 matingly engages the predetermined surface region on the scapula 71. The first cutting tool template 200 includes a post 224 extending away (in a distal direction) from the patient specific bone contacting surface 216. The post 224 ensures stability and rotational control for bone preparation.

In one implementation, a longitudinal axis of the locating pin hole 202 is directed into a base of a coracoid 74 of the scapula 71 when the patient specific bone contacting surface 216 matingly engages the predetermined surface region on the scapula 71. The patient specific bone contacting surface 216 has a complementary shape to a bone surface of the three-dimensional model 70 of the scapula 71 of the patient reconstructed from image scans of the scapula 71 of the patient. The first cutting tool template 200 can be fabricated using 3D printing based on the three-dimensional model 70 of the scapula 71 of the patient.

In a fourth step of the method, a second cutting tool template 300 is fabricated. Referring now to FIG. 7, the second cutting tool template 300 has a locating pin hole 302 dimensioned to receive the coracoid pin 116, a plurality of cutting guide slots 311, 312, 313, 314, 315 dimensioned to receive a cutting tool, and a patient specific bone contacting surface 316. The patient specific bone contacting surface 316 is configured to contact the scapula 71 for ensuring a custom fit of the second cutting tool template 300 and a predetermined region on the scapula 71. The custom fit of the cutting tool template 300 and the predetermined surface region on the scapula 71 extends from a first border 318 of the cutting tool template 300 across an inner region 320 of the second cutting tool template 300 to a second border 322 of the cutting tool template 300. The second cutting tool template 300 is dimensioned such that an inner surface of the locating pin hole 302 is spaced apart from the predetermined surface region on the scapula 71 when the patient specific bone contacting surface 316 matingly engages the predetermined surface region on the scapula 71. The cutting tool template 300 includes a post (similar to 224 in FIG. 9) extending away from the patient specific bone contacting surface 316.

In one implementation, a longitudinal axis of the locating pin hole 302 is directed into a base of a coracoid 74 of the scapula 71 when the patient specific bone contacting surface 316 matingly engages the predetermined surface region on the scapula 71. The patient specific bone contacting surface 316 has a complementary shape to a bone surface of the three-dimensional model 70 of the scapula 71 of the patient reconstructed from image scans of the scapula 71 of the patient. The second cutting tool template 300 can be fabricated using 3D printing based on the three-dimensional model 70 of the scapula 71 of the patient.

In a fifth step of the method, a third cutting tool template 400 is fabricated. Referring now to FIG. 8, the third cutting tool template 400 has a locating pin hole 402 dimensioned to receive the coracoid pin 116, a plurality of cutting guide slots 411, 412 dimensioned to receive a cutting tool, and a patient specific bone contacting surface 416. The patient specific bone contacting surface 416 is configured to contact the scapula 71 for ensuring a custom fit of the third cutting tool template 400 and a predetermined region on the scapula 71. The custom fit of the cutting tool template 400 and the predetermined surface region on the scapula 71 extends from a first border 418 of the cutting tool template 400 across an inner region 420 of the cutting tool template 400 to a second border 422 of the third cutting tool template 400. The third cutting tool template 400 is dimensioned such that an inner surface of the locating pin hole 402 is spaced apart from the predetermined surface region on the scapula 71 when the patient specific bone contacting surface 416 matingly engages the predetermined surface region on the scapula 71. The cutting tool template 400 includes a post (similar to 224 in FIG. 9) extending away from the patient specific bone contacting surface 416.

In one implementation, a longitudinal axis of the locating pin hole 402 is directed into a base of a coracoid 74 of the scapula 71 when the patient specific bone contacting surface 416 matingly engages the predetermined surface region on the scapula 71. The patient specific bone contacting surface 416 has a complementary shape to a bone surface of the three-dimensional model 70 of the scapula 71 of the patient reconstructed from image scans of the scapula 71 of the patient. The third cutting tool template 400 can be fabricated using 3D printing based on the three-dimensional model 70 of the scapula 71 of the patient.

Although the implementations shown and described above include a plurality of cutting guide slots, alternative implementations may include one or more cutting guide slots.

Figure 11:
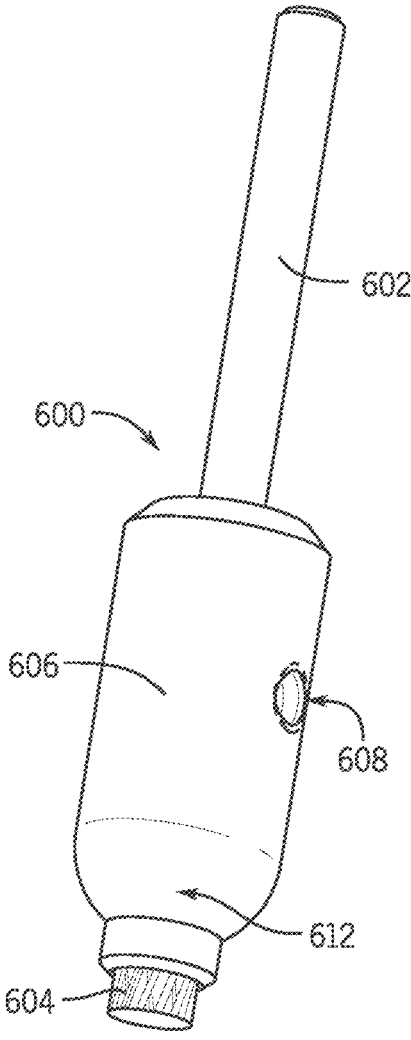
FIG. 11 is a perspective view of a cutting tool according to one example implementation of the present disclosure.

Looking now at FIG. 11, the method uses a cutting tool 600 that is dimensioned for insertion into each of the plurality of cutting guide slots 211, 212, 213, 214, 311, 312, 313, 314, 315, 411, 412 of the cutting templates 200, 300, 400 to remove a portion of the surface of the scapula 71. The cutting tool 600 has a shank 602 that terminates in cutting surfaces 604. The shank 602 can be mounted in a chuck of a drill for rotation as is known in the art. The cutting tool 600 includes a cutting depth sleeve 606 positioned on the shank 602 by a set screw 608 that enables the cutting depth sleeve

606 to be positioned at different locations of the shank 602. A distal surface 612 of the cutting depth sleeve 606 contacts a proximal surface 232, 332, 432 of each of the cutting tool templates 200, 300, 400 to limit a cutting depth of the cutting tool 600 in the scapula 71. By varying the contours of the proximal surface 232, 332, 432 of each of the cutting tool templates 200, 300, 400, a uniform depth bone preparation can be prepared in the scapula 71.

In the method, the first cutting tool template 200 is positioned such that the coracoid pin 116 is located in the locating pin hole 202, the post 224 is located in the positioning hole 144 (see FIG. 24), and the patient specific bone contacting surface 216 matingly engages a predetermined surface region on the scapula 71. The cutting tool 600 is sequentially inserted into each of the plurality of cutting guide slots 211, 212, 213, 214 and the cutting tool 600 is activated such that the cutting tool 600 removes surface portions of the scapula 71 creating a first part of a bone preparation in the scapula 71. The cutting tool 600 and the first cutting tool template 200 are then disengaged from the scapula 71.

The second cutting tool template 300 is then positioned such that the coracoid pin 116 is located in the locating pin hole 302, the post is located in the positioning hole 144 (see FIG. 24), and the patient specific bone contacting surface 316 matingly engages a predetermined surface region on the scapula 71. The cutting tool 600 is sequentially inserted into each of the plurality of cutting guide slots 311, 312, 313, 314, 315 and the cutting tool 600 is activated such that the cutting tool 600 removes surface portions of the scapula 71 creating a second part of a bone preparation in the scapula 71. The cutting tool 600 and the second cutting tool template 300 are then disengaged from the scapula 71.

The third cutting tool template 400 is then positioned such that the coracoid pin 116 is located in the locating pin hole 402, the post is located in the positioning hole 144 (see FIG. 24), and the patient specific bone contacting surface 416 matingly engages a predetermined surface region on the scapula 71. The cutting tool 600 is sequentially inserted into each of the plurality of cutting guide slots 411, 412 and the cutting tool 600 is activated such that the cutting tool 600 removes surface portions of the scapula 71 creating a third part of a bone preparation in the scapula 71. The cutting tool 600 and the third cutting tool template 400 are then disengaged from the scapula 71. The distal surface 612 of the cutting depth sleeve and the proximal surfaces 232, 332, 432 of each of the cutting tool templates 200, 300, 400 are shaped in a complementary manner such that a uniform depth of the surface of the scapula 71 is removed.

Figure 13:
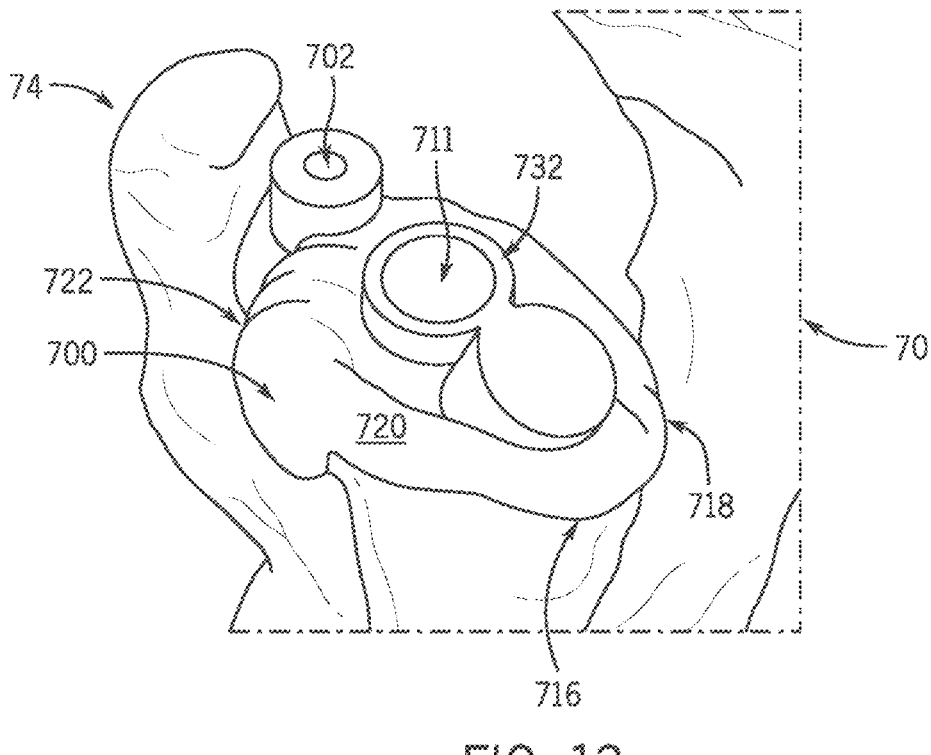
FIG. 13 is a perspective view of a fourth cutting tool template according to one example implementation of the present disclosure positioned on a scapula.

In a sixth step of the method, a fourth cutting tool template 700 is fabricated. Referring now to FIG. 13, the fourth cutting tool template 700 has a locating pin hole 702 dimensioned to receive the coracoid pin 116, a cutting guide aperture 711 dimensioned to receive a cutting tool, and a patient specific bone contacting surface 716. The patient specific bone contacting surface 716 is configured to contact the scapula 71 for ensuring a custom fit of the fourth cutting tool template 700 and a predetermined region on the scapula 71. The custom fit of the fourth cutting tool template 700 and the predetermined surface region on the scapula 71 extends from a first border 718 of the cutting tool template 700 across an inner region 720 of the cutting tool template 700 to a second border 722 of the fourth cutting tool template 700. The fourth cutting tool template 700 is dimensioned such that an inner surface of the locating pin hole 702 is spaced apart from the predetermined surface region on the scapula 71 when the patient specific bone contacting surface 716 matingly engages the predetermined surface region on the scapula 71. The glenoid pin 114 is re-inserted through into the glenoid cavity. The fourth cutting tool template 700 can be fabricated using 3D printing based on the three-dimensional model 70 of the scapula 71 of the patient.

Figure 12:
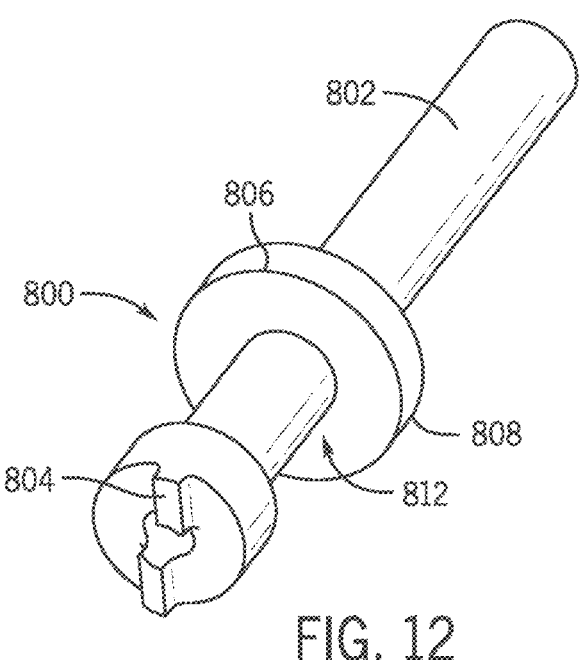
FIG. 12 is a perspective view of a reamer according to one example implementation of the present disclosure.

Looking now at FIG. 12, the method uses a cannulated reamer 800 that is dimensioned for insertion into the cutting guide aperture 711 of the fourth cutting template 700 to remove a portion of the surface of the scapula 71. The cannulated reamer 800 has a shank 802 that terminates in cutting surfaces 804. The shank 802 can be mounted in a chuck of a drill for rotation as is known in the art. The cannulated reamer 800 includes a cutting depth sleeve 806 positioned on the shank 802 by a set screw 808 that enables the cutting depth sleeve 806 to be positioned at different locations of the shank 802. A distal surface 812 of the cutting depth sleeve 806 contacts a proximal surface 732 of the cutting tool template 700 to limit a cutting depth of the cannulated reamer 800 in the scapula 71.

In the method, the fourth cutting template 700 is positioned such that the coracoid pin 116 is located in the locating pin hole 702, the glenoid pin 114 is placed in positioning hole 144, and the patient specific bone contacting surface 716 matingly engages a predetermined surface region on the scapula 71. The cannulated reamer 800 is inserted into cutting guide aperture 711 over the glenoid pin 114 and the cannulated reamer 800 is activated such that the cannulated reamer 800 removes surface portions of the scapula 71 creating a fourth part of a bone preparation in the scapula 71. The cannulated reamer 800 and the fourth cutting template 700 are then disengaged from the scapula 71. The distal surface 812 of the cannulated reamer 800 and the proximal surface 732 of the fourth cutting template 700 are shaped in a complementary manner such that a uniform depth of the surface of the scapula 71 is removed.

Figure 14:
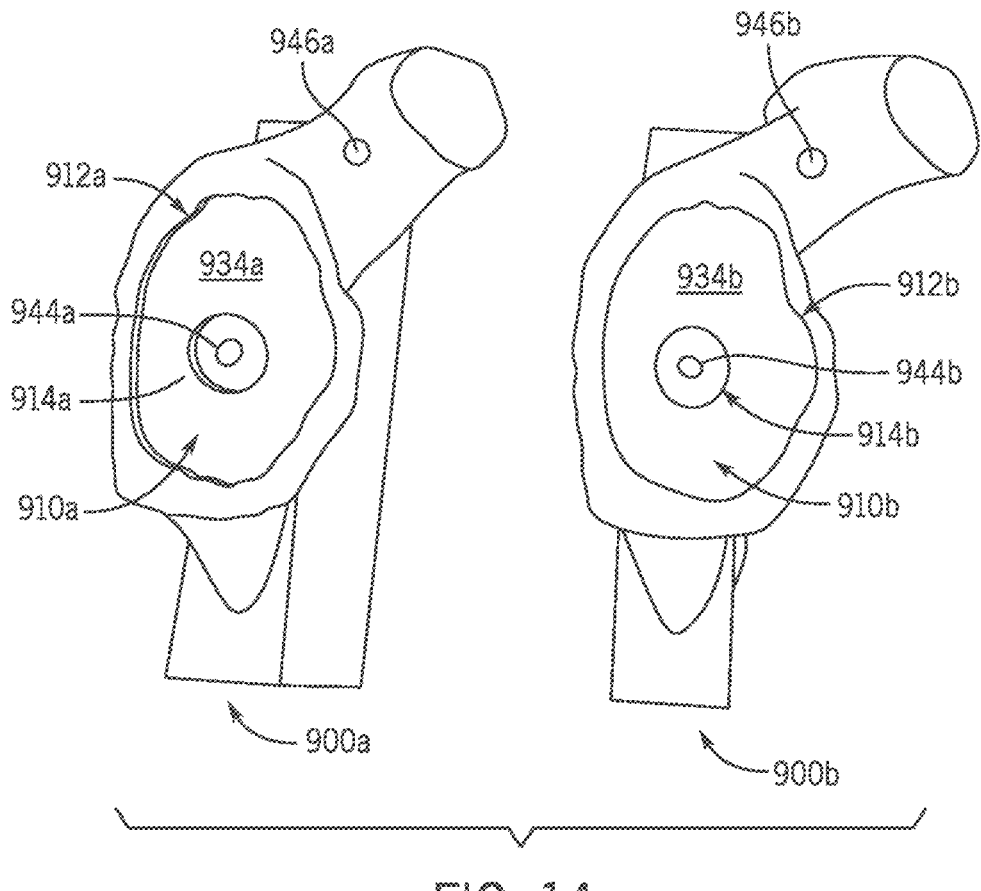
FIG. 14 is a lateral view of non-limiting example physical scapula models prepared in accordance with the methodology of this disclosure.
Figure 15:
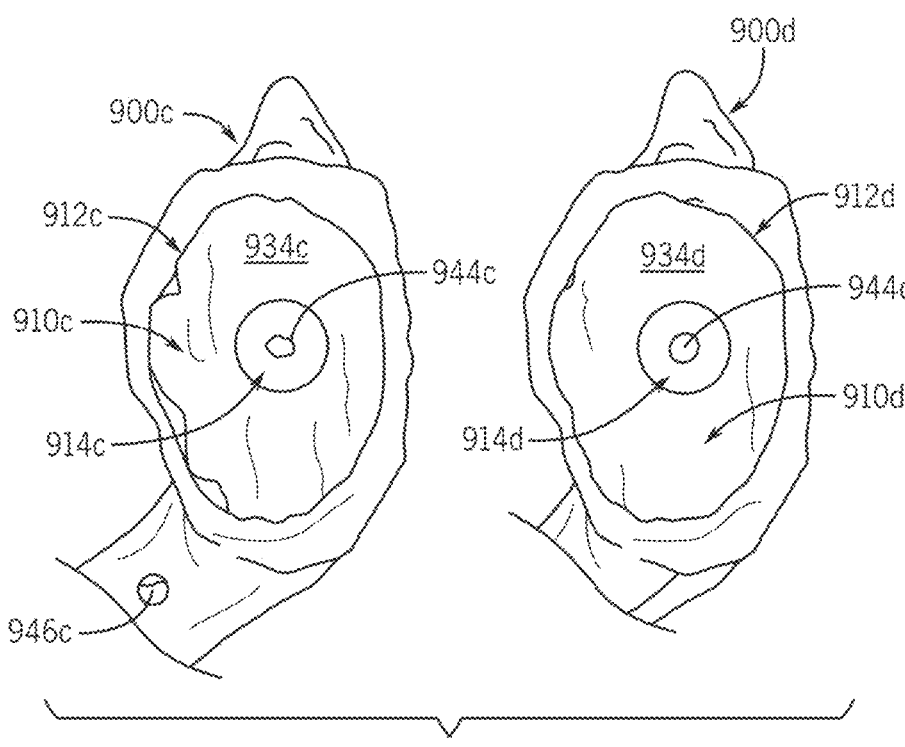
FIG. 15 is a lateral view of a non-limiting example physical scapula models prepared in accordance with the methodology of this disclosure.
Figure 16:
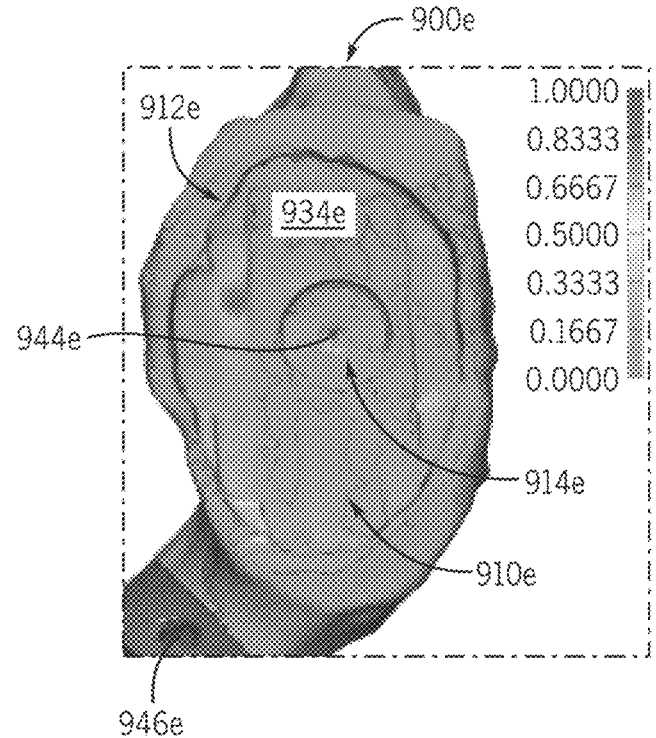
FIG. 16 is a lateral view of a non-limiting example physical scapula model showing the difference in depths of the models shown in FIGS. 14 and 15 prepared in accordance with the methodology of this disclosure.
Figure 17:
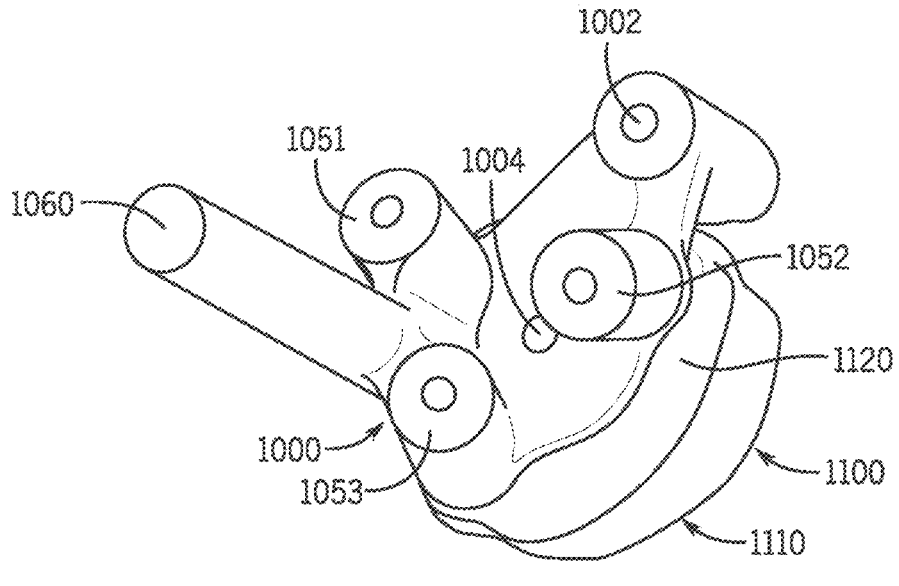
FIG. 17 is a perspective view of an insertion instrument according to one example implementation of the present disclosure positioned on a glenoid baseplate.
Figure 18:
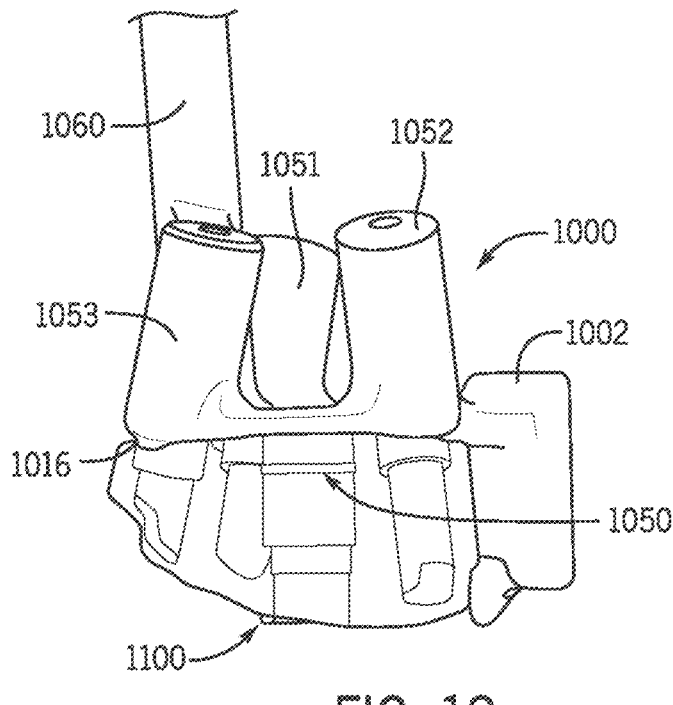
FIG. 18 is a side view of the insertion instrument of FIG. 17 positioned on a glenoid baseplate.

Looking at FIGS. 14, 15, and 16, there are shown non-limiting example physical scapula models 900a, 900b, 900c, 900d, 900e with a uniform depth bone preparations 910a, 910b, 910c, 910d, 910e in the scapula 71 created through use of the locating pin guide 100, the glenoid pin 114, the coracoid pin 116, the first cutting tool template 200, the second cutting tool template 300, the third cutting tool template 400, the cutting tool 600, the fourth cutting tool template 700, and the cannulated reamer 800 in the method described above. FIGS. 14, 15, and 16 confirm that the method creates predictable and reproducible bone preparation.

Looking at FIG. 14, the uniform depth bone preparation 910a in the scapula model 900a includes a bone preparation proximal perimeter edge 912a formed by the use of the cutting tool 600 and the cutting templates 200, 300, 400, an inner depression 914a formed by the cannulated reamer 800 in the inner surface 934a, and a positioning hole 944a formed by the glenoid pin 114. The scapula model 900a also has a locating hole 946a formed by the coracoid pin 116.

Looking at FIG. 14, the uniform depth bone preparation 910b in the scapula model 900b includes a bone preparation proximal perimeter edge 912b formed by the use of the cutting tool 600 and the cutting templates 200, 300, 400, an inner depression 914b formed by the cannulated reamer 800 in the inner surface 934b, and a positioning hole 944b formed by the glenoid pin 114. The scapula model 900b also has a locating hole 946b formed by the coracoid pin 116.

Looking at FIG. 15, the uniform depth bone preparation 910c in the scapula model 900c includes a bone preparation proximal perimeter edge 912c formed by the use of the cutting tool 600 and the cutting templates 200, 300, 400, an inner depression 914c formed by the cannulated reamer 800 in the inner surface 934c, and a positioning hole 944c formed by the glenoid pin 114. The scapula model 900c also has a locating hole 946c formed by the coracoid pin 116.

Looking at FIG. 15, the uniform depth bone preparation 910d in the scapula model 900d includes a bone preparation proximal perimeter edge 912d formed by the use of the cutting tool 600 and the cutting templates 200, 300, 400, an inner depression 914d formed by the cannulated reamer 800 in the inner surface 934d, and a positioning hole 944d formed by the glenoid pin 114.

FIG. 16 shows that a consistent depth of bone preparation was achieved for a significant portion of the prepared bone models 900a, 900b, 900c, 900d shown in FIGS. 14 and 15. The scale is in fraction of a 1 millimeter. FIG. 16 shows that a significant portion (e.g., over 95%) of the bone preparation had a consistent depth of bone removal within 1 mm or less. The uniform depth bone preparation 910e in the scapula model 900e includes a bone preparation proximal perimeter edge 912e formed by the use of the cutting tool 600 and the cutting templates 200, 300, 400, an inner depression 914e formed by the cannulated reamer 800 in the inner surface 934e, and a positioning hole 944e formed by the glenoid pin 114. The scapula model 900e also has a locating hole 946e formed by the coracoid pin 116.

By "uniform depth", it is meant that the depth from locations around the bone preparation proximal perimeter edges 912a, 912b, 912c, 912d, 912e to the inner surfaces 934a, 934b, 934c, 934d, 934e of the bone preparations 910a, 910b, 910c, 910d, 910e has a depth tolerance of ±30%, preferably ±20%, more preferably ±10%, and most preferably ±5%. The staggered cutting templates 200, 300, 400 provide a stable platform for bone removal and can remove uniform depth of bone on an irregular surface. In some implementations, the pre-determined amount of bone removed may be uniform, which may be the most efficient and common scenario. However, it is not mandatory for the amount of bone removed to be uniform. Based on the underlying bone architecture, one could specifically plan that more bone is removed in one section compared to another.

Figure 37:
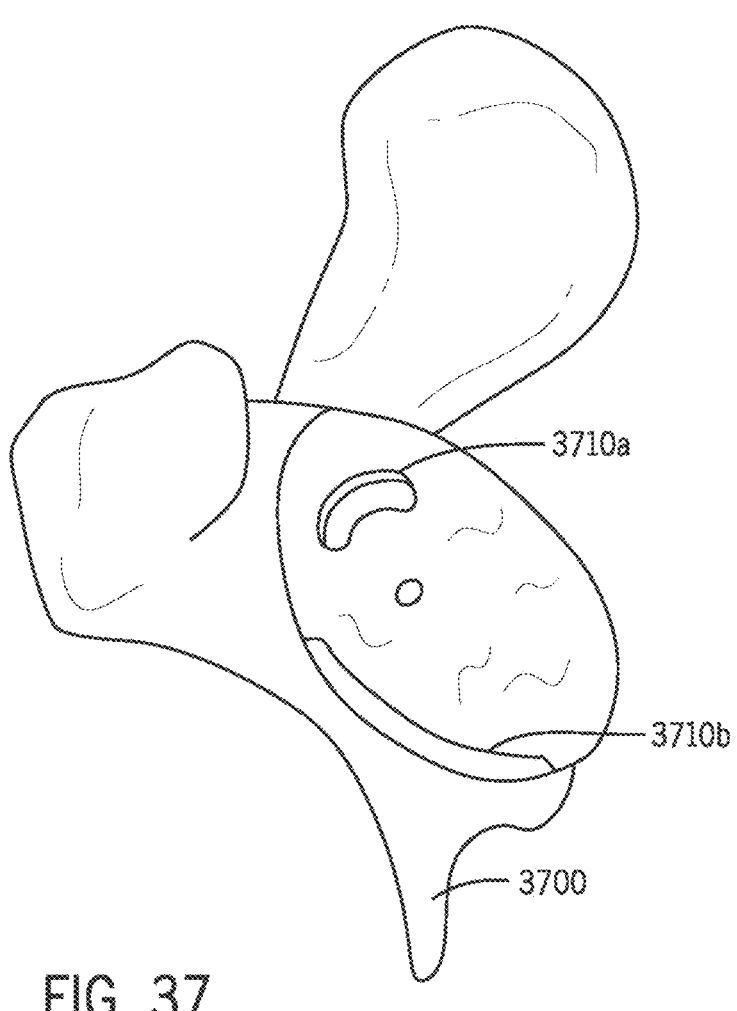
FIG. 37 is a perspective view of a non-limiting example physical scapula model prepared in accordance with the methodology of this disclosure.

For example, as shown in FIG. 37, the depth of bone removed in a first section 3710a of the bone 3700 is deeper than the depth of the bone removed in a second section 3710b of the bone 3700. The first section 3710a is a recess defined inwardly and spaced apart from the peripheral edge of the glenoid cavity. The second section 3710b is a recessed surface contour defined along the peripheral edge of the glenoid cavity. As shown, the first section 3710a and second section 3710b are spaced apart from each other, but in other implementations, the first and second sections of bone to be removed may be contiguous.

Figure 39:
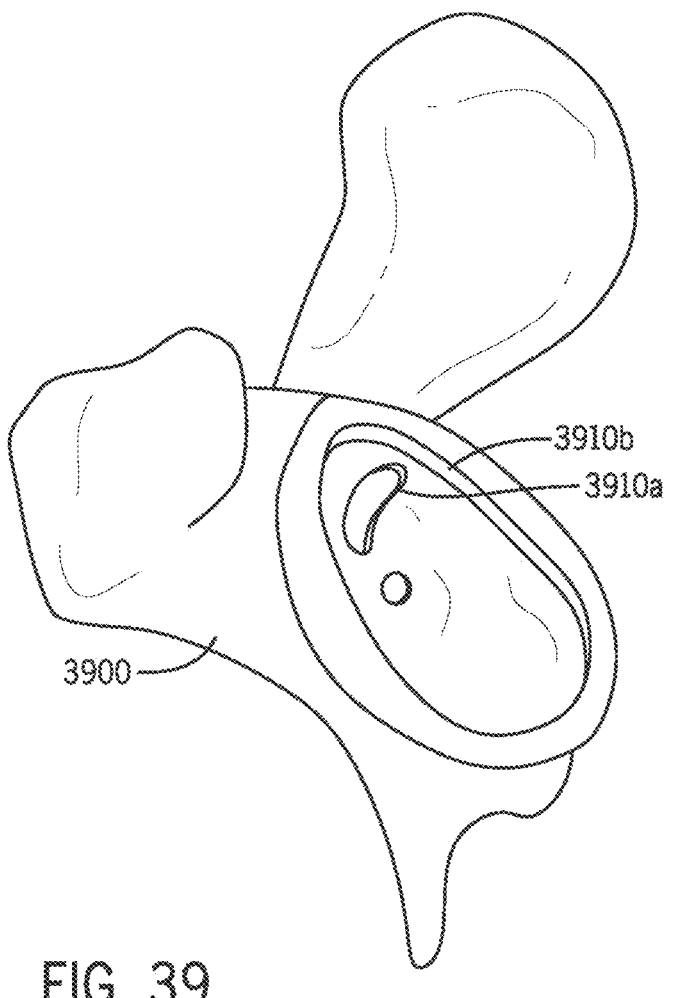
FIG. 39 is a perspective view of a non-limiting example physical scapula model prepared in accordance with the methodology of this disclosure.

FIG. 39 shows another alternative implementation similar to the implementation in FIG. 37, which includes bone 3900, a first section 3910a of bone removed, and a second section 3910b of bone removed. The first section 3910a is a recess defined inwardly and spaced apart from the peripheral edge of the glenoid cavity. The second section 3910b is a recessed surface contour defined along the peripheral edge of the glenoid cavity and extends further along the peripheral edge than the second section 3710b shown in FIG. 37.

Figure 41:
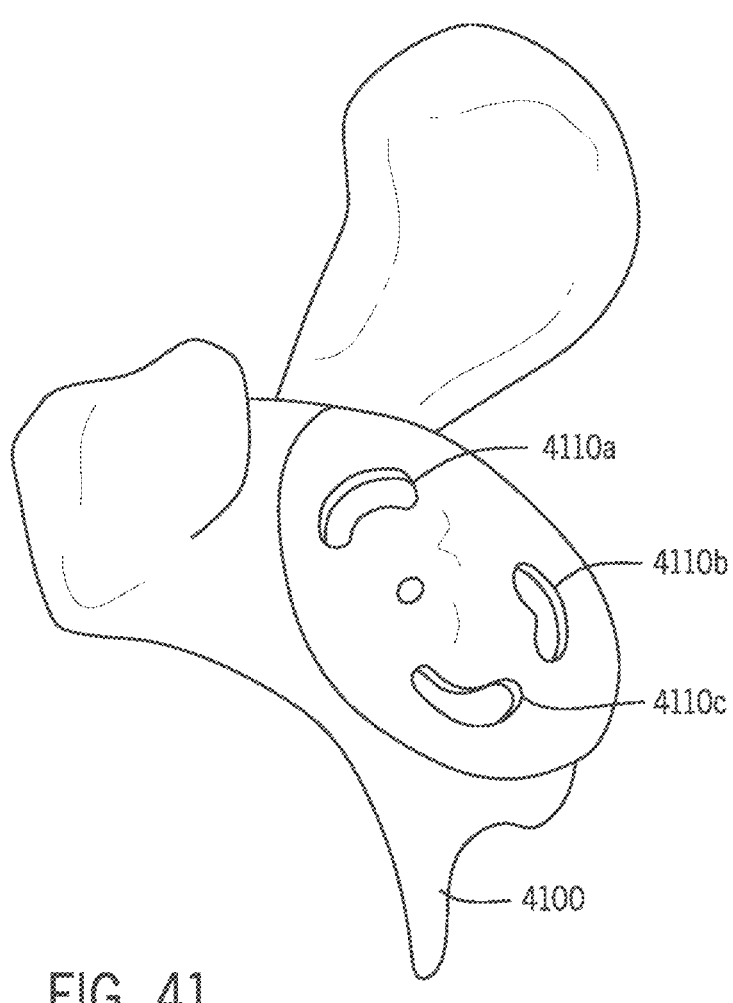
FIG. 41 is a perspective view of a non-limiting example physical scapula model prepared in accordance with the methodology of this disclosure.

FIG. 41 shows another alternative implementation, which includes bone 4100, a first section 4110a of bone removed, a second section 4110b of bone removed, and a third section 4110c of bone removed. The sections 4110a, 4110b, 4110c are recesses and are disposed inwardly and spaced apart from the peripheral edge of the glenoid cavity. In addition, the sections 4110*a*, 4110*b*, 4110*c* are spaced apart circumferentially from each other (e.g., evenly spaced apart as measured from a center of each section). In this implementation, there is no bone material removed at the peripheral edge of the glenoid cavity.

Figure 43:
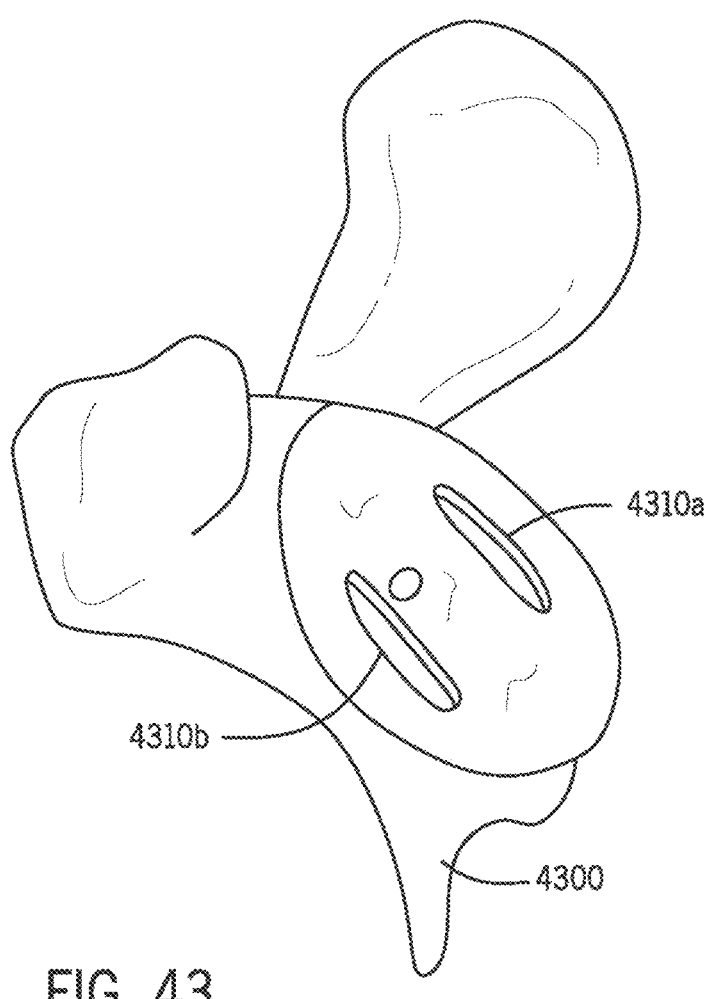
FIG. 43 is a perspective view of a non-limiting example physical scapula model prepared in accordance with the methodology of this disclosure.

FIG. 43 shows another alternative implementation, which includes bone 4300, a first section 4310*a* of bone removed and a second section 4310*b* of bone removed. The sections 4310*a*, 4310*b* are recesses and are disposed inwardly and spaced apart from the peripheral edge of the glenoid cavity. In addition, the sections 4310*a*, 4310*b* are disposed on opposite sides of the glenoid cavity (e.g., diametrically opposed from each other). In this implementation, there is no bone material removed at the peripheral edge.

Figure 45:
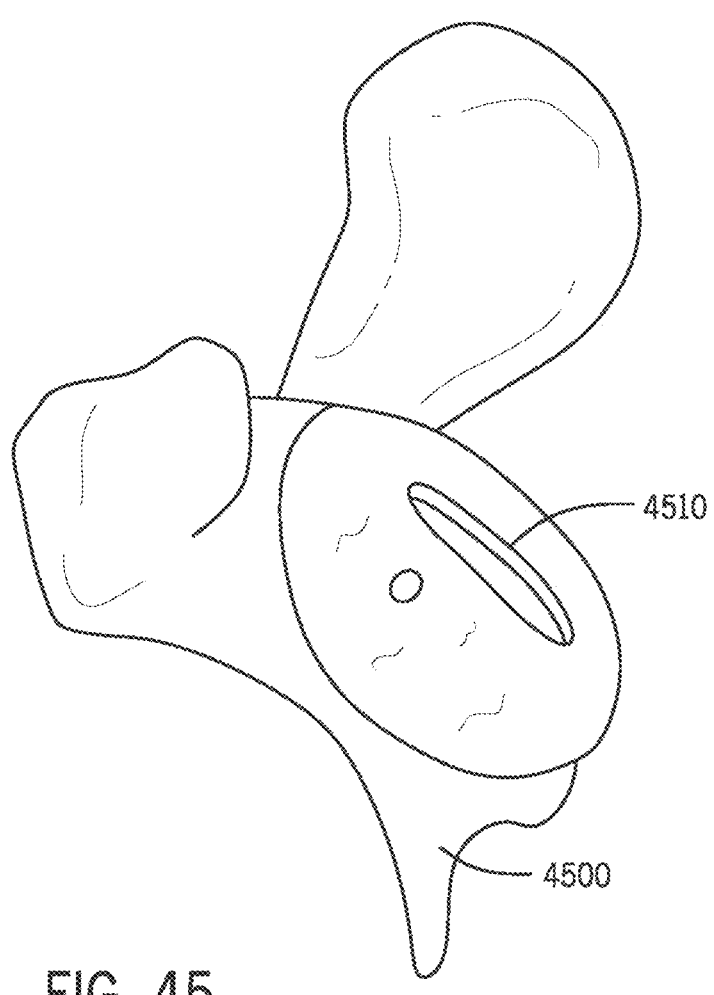
FIG. 45 is a perspective view of a non-limiting example physical scapula model prepared in accordance with the methodology of this disclosure.

FIG. 45 shows another alternative implementation, which includes bone 4500 and one section 4510 of bone removed. The section 4510 is a recess that is disposed inwardly and spaced apart from the peripheral edge of the glenoid cavity. In this implementation, there is no bone material removed at the peripheral edge.

In the implementations described above, the cutting tool 600 is inserted into each of the cutting guide slots on the cutting tool templates. However, in other implementations, the cutting tool, such as cutting tool 600, may be inserted into one or more of the cutting guide slots of the cutting tool template(s) (e.g., the cutting tool templates shown in FIGS. 22-29) to customize the size and/or shape of the bone preparation area desires. For example, the cutting tool 600 be inserted into one or more slots of a cutting tool templates, such as the cutting tool templates shown in FIGS. 22-29 or other cutting tool templates that define slot(s) in the desired location(s), to create the bone preparation shown in FIGS. 37, 39, 41, 43, and/or 45.

In addition, in other implementations, the bone preparation may include any combination of the recesses and/or recessed surface contours described and shown herein. For example, the bone preparation may include one or more recesses and/or recessed surface contours defined inwardly and spaced apart from a peripheral edge of the bone and/or one or more recessed surface contours and/or recesses defined along or directly adjacent to at least a portion of the peripheral edge of the bone.

In a seventh step of the method, a glenoid component 1100 (e.g., a glenoid baseplate), and optionally, an insertion instrument 1000, is fabricated. The implementation shown in FIGS. 17-20 includes the insertion instrument 1000 and the component 1100. As shown, the insertion instrument 1000 has a locating pin hole 1002, which is dimensioned to receive the coracoid pin 116, and a component contacting surface 1016, wherein the component contacting surface 1016 is configured to contact the glenoid component 1100 for ensuring a custom fit of the glenoid component contacting surface 1016 and a first superficial proximal surface 1120 of the glenoid component 1100. The insertion instrument 1000 and the glenoid component 1100 can be fabricated using 3D printing based on a three-dimensional model of the scapula 71 of the patient reconstructed from image scans of the scapula of the patient. The insertion instrument 1000 is dimensioned such that an inner surface of the locating pin hole 1002 is spaced apart from the predetermined surface region on the scapula 71 when a patient specific bone contacting surface 1110 of the glenoid component 1100 matingly engages a predetermined surface region on the scapula 71. The insertion instrument 1000 includes an additional locating pin hole 1004 dimensioned to receive the glenoid pin 114, and a longitudinal axis of the additional locating pin hole 1004 is directed into a glenoid cavity of the scapula 71 spaced inward from a perimeter of the scapula 71 when the patient specific bone contacting surface 1110 of the glenoid component 1100 matingly engages the predetermined surface region on the scapula 71. The insertion instrument 1000 includes a plurality of tubular screw guides 1051, 1052, 1053 radially spaced outward from the additional locating pin hole 1004, and a handle 1060. The glenoid component 1100 includes a plurality of tubular screw receiving holes 1151, 1152, 1153 radially spaced outward from a tubular inset 1104. Screws or other suitable fixation devices, such as pins or post(s), may be engaged through the screw receiving holes 1151, 1152, 1153 to couple the glenoid component 1100 to the patient's bone. A stabilizer, such as O-ring 1050, is dimension to engage the glenoid component 1100 and the insertion instrument 1000. The inset 1104 can be dimensioned to receive in an interference fit: (i) a concave polymeric glenoid liner for articulation with a hemispherical head of a humeral component in a total shoulder prosthesis, or (ii) a glenosphere implant including a convex section that articulates with a complementary concave section of the head of the humeral component in a reverse shoulder prosthesis. The glenoid component 1100 is manufactured with a protrusion 1177 that extends from a peripheral edge 1178 of a proximal section 1175 distally toward the patient specific bone contacting surface 1110 of the glenoid component 1100 (see FIG. 20). The protrusion 1177 has a length measured proximally to distally that corresponds to the depth of bone removed from the scapula 71 and a shape corresponding to the shape of the bone preparation. The glenoid component 1100 is also manufactured with a peripheral stabilizing flange 1179.

Figure 21:
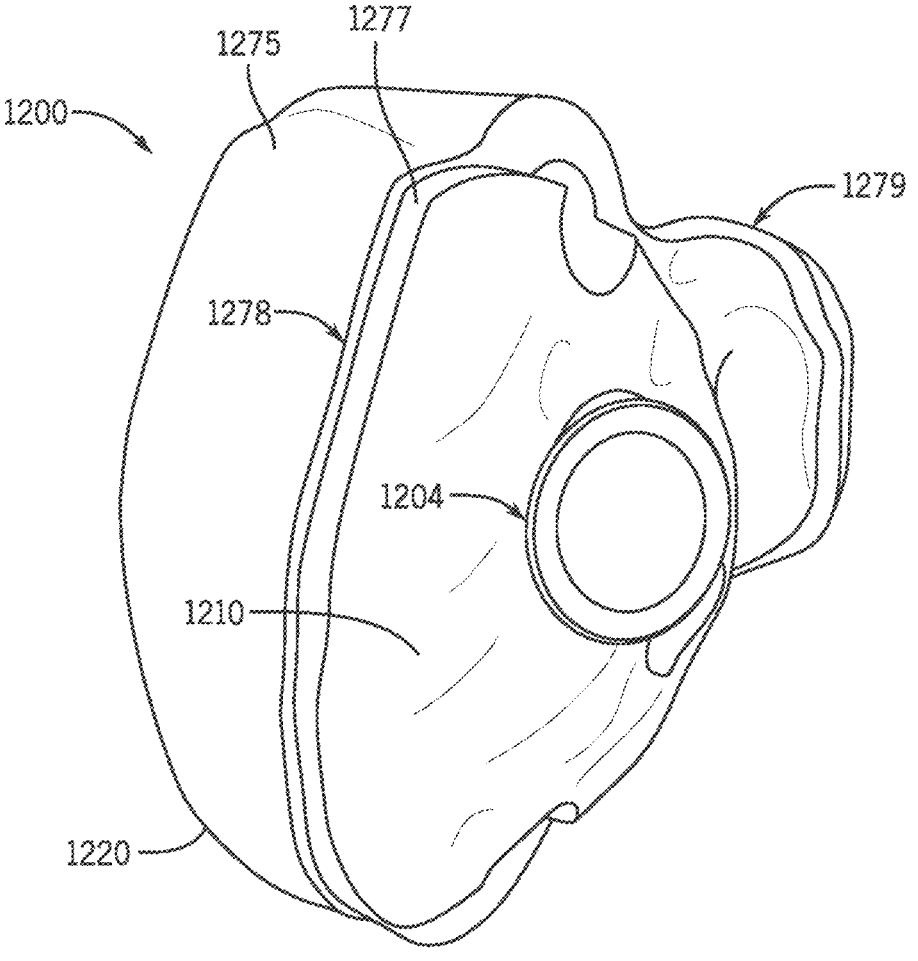
FIG. 21 is a perspective view of a glenoid baseplate according to another example implementation of the present disclosure.

In an alternative implant design shown in FIG. 21, a glenoid component 1200 includes an additional inset 1204. The glenoid component 1200 is manufactured with a first superficial proximal surface 1220 and with a protrusion 1277 that extends from a peripheral edge 1278 of a proximal section 1275 distally toward the patient specific bone contacting surface 1210 of the glenoid component 1200 (see FIG. 21). The protrusion 1277 has a length measured proximally to distally that corresponds to the depth of bone removed from the scapula 71 and a shape corresponding to the shape of the bone preparation. The glenoid component 1200 is also manufactured with a peripheral stabilizing flange 1279. Thus, the glenoid components 1100 and 1200 can be manufactured with a protrusion 1177, 1277 length that corresponds to the planned depth of bone removal. The manufacturer (e.g., 3D printing fabricator) can decide the exact depth of bone removal and the corresponding length of protrusion to add to the implant. The length of the protrusion in this example was 2 mm that matched the depth of bone removal. Some manufacturers may prefer to add an additional length of implant thickness from compaction during insertion. However, as noted above it is a possibility that more bone can be removed in some sections compared to others. Therefore, the protrusion 1177, 1277 does not necessarily have to be a uniform length measured proximally to distally.

Figure 20:
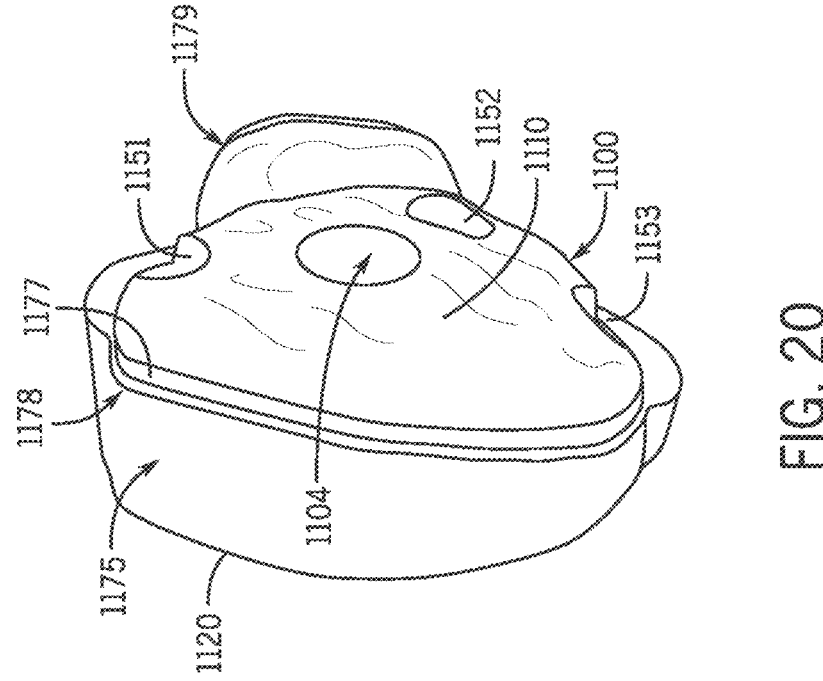
FIG. 20 is a side view of the glenoid baseplate of FIG. 19.
Figure 19:
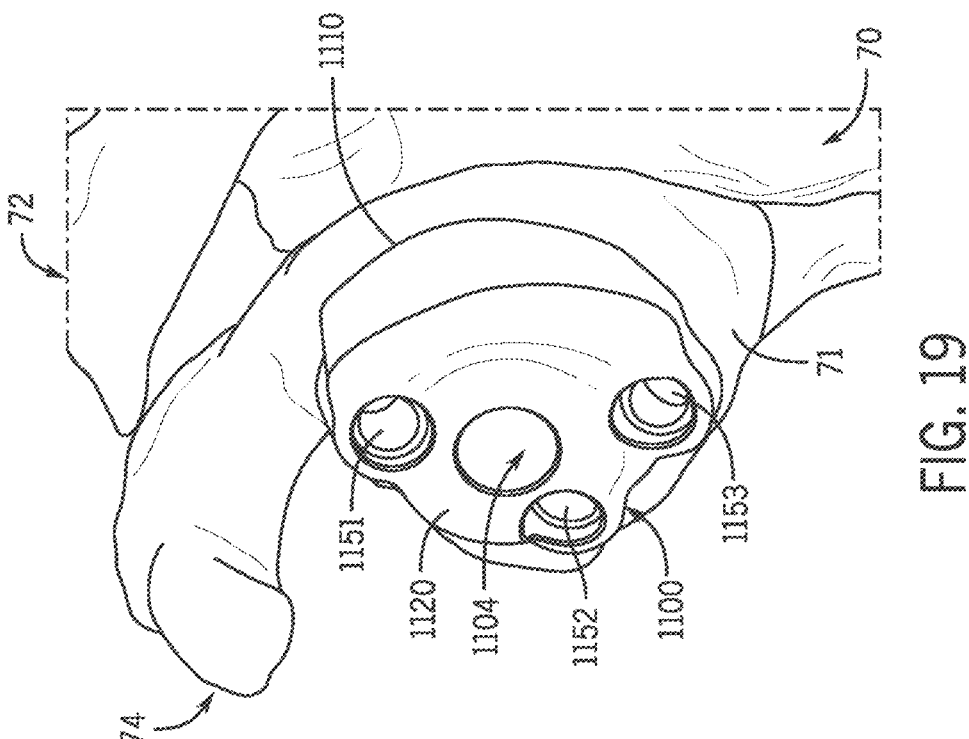
FIG. 19 is a perspective view of a glenoid baseplate according to one example implementation of the present disclosure positioned on a scapula.

The implementations shown in FIGS. 20 and 21 include protrusions 1177, 1277 that extend from the peripheral edges 1178, 1278 of the proximal sections 1175, 1275 toward the patient specific bone contacting surfaces 1110, 1210 of the glenoid components 1100, 1200, respectively. However, in other implementations, the protrusions of the component may include one or more protrusions that are disposed inwardly and spaced apart from the peripheral edge of the proximal section of the component and/or may extend from one or more portions of the peripheral edge of the proximal section of the component.

Figure 38:
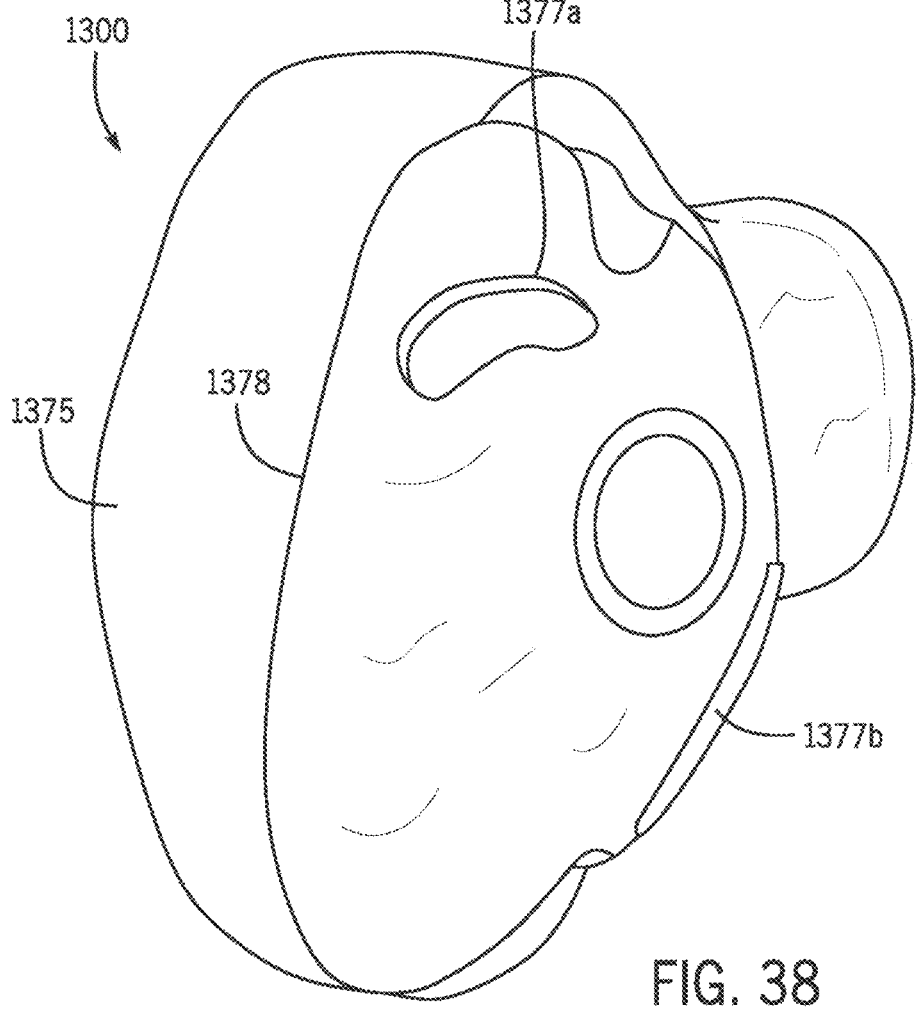
FIG. 38 is a perspective view of a glenoid baseplate according to another implementation that is configured for engaging with the physical scapula model shown in FIG. 37.

For example, in the implementation shown in FIG. 38, the glenoid component 1300 is manufactured with a first protrusion 1377a and a second protrusion 1377b. The first protrusion 1377a extends from a portion of the patient specific bone contacting surface 1310 of the glenoid component 1300 and is disposed inwardly and spaced apart from the peripheral edge 1378 of the proximal section 1375 of the glenoid component 1300. The second protrusion 1377b extends from a portion of the peripheral edge 1378 of the proximal section 1375 of the glenoid component 1300 toward the patient specific bone contacting surface 1310. The first protrusion 1377a has a length that is greater than a length of the second protrusion 1377b, wherein the length is measured from a proximal end of the protrusion to a distal end of the protrusion. The first protrusion 1377a is configured to engage the recess 3710a defined in bone 3700 shown in FIG. 37, and the second protrusion 1377b is configured to engage the recessed surface contour 3710b defined in bone 3700 shown in FIG. 37. Thus, glenoid component 1300 shown in FIG. 38 is configured to engage the bone 3700 shown in FIG. 37.

Figure 40:
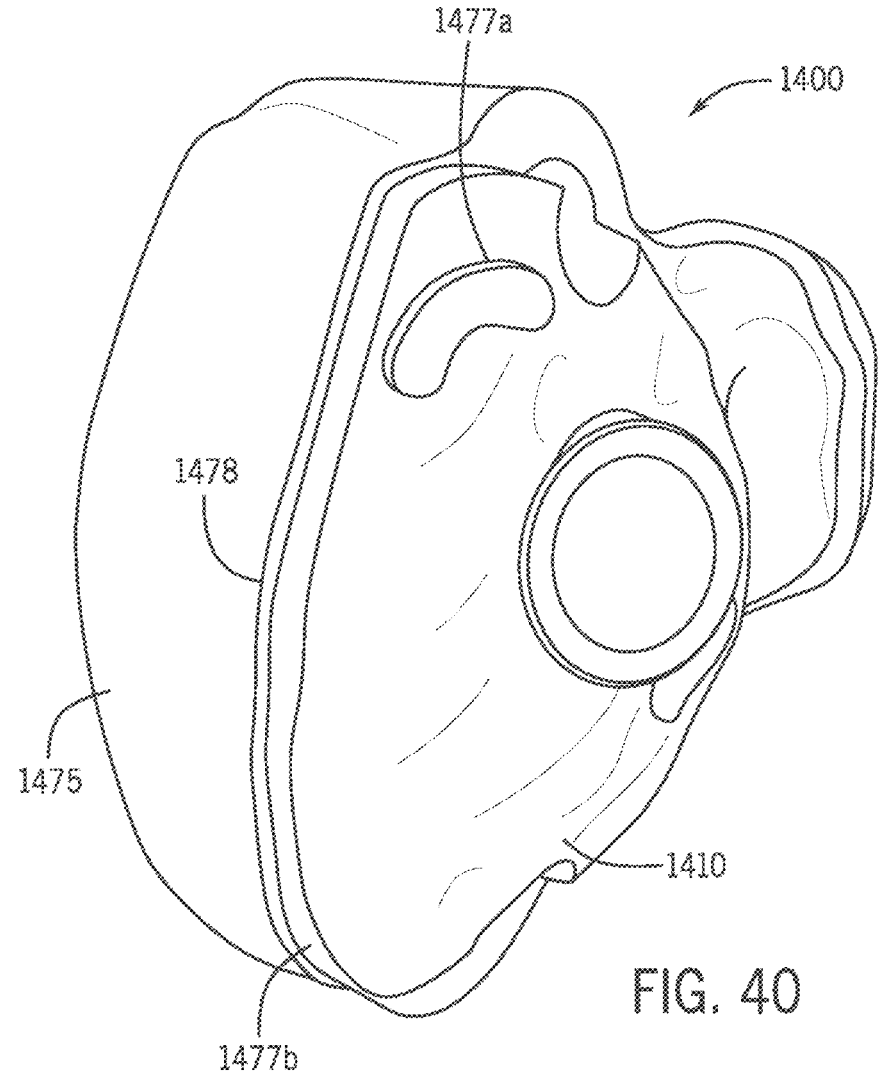
FIG. 40 is a perspective view of a glenoid baseplate according to another implementation that is configured for engaging with the physical scapula model shown in FIG. 39.

As another example, in the implementation shown in FIG. 40, the glenoid component 1400 is manufactured with a first protrusion 1477a and a second protrusion 1477b. The first protrusion 1477a extends from a portion of the patient specific bone contacting surface 1410 of the glenoid component 1400 and is disposed inwardly and spaced apart from the peripheral edge 1478 of the proximal section 1475 of the glenoid component 1400. The second protrusion 1477b extends from the peripheral edge 1478 of the proximal section 1475 of the glenoid component 1400. The first protrusion 1477a has a length that is greater than a length of the second protrusion 1477b, wherein the length is measured from a proximal end of the protrusion to a distal end of the protrusion. The first protrusion 1477a is configured to engage the recess 3910a defined in bone 3900 shown in FIG. 39, and the second protrusion 1477b is configured to engage the recessed surface contour 3910b defined in bone 3900 shown in FIG. 39. Thus, glenoid component 1400 shown in FIG. 40 is configured to engage the bone 3900 shown in FIG. 39.

Figure 42:
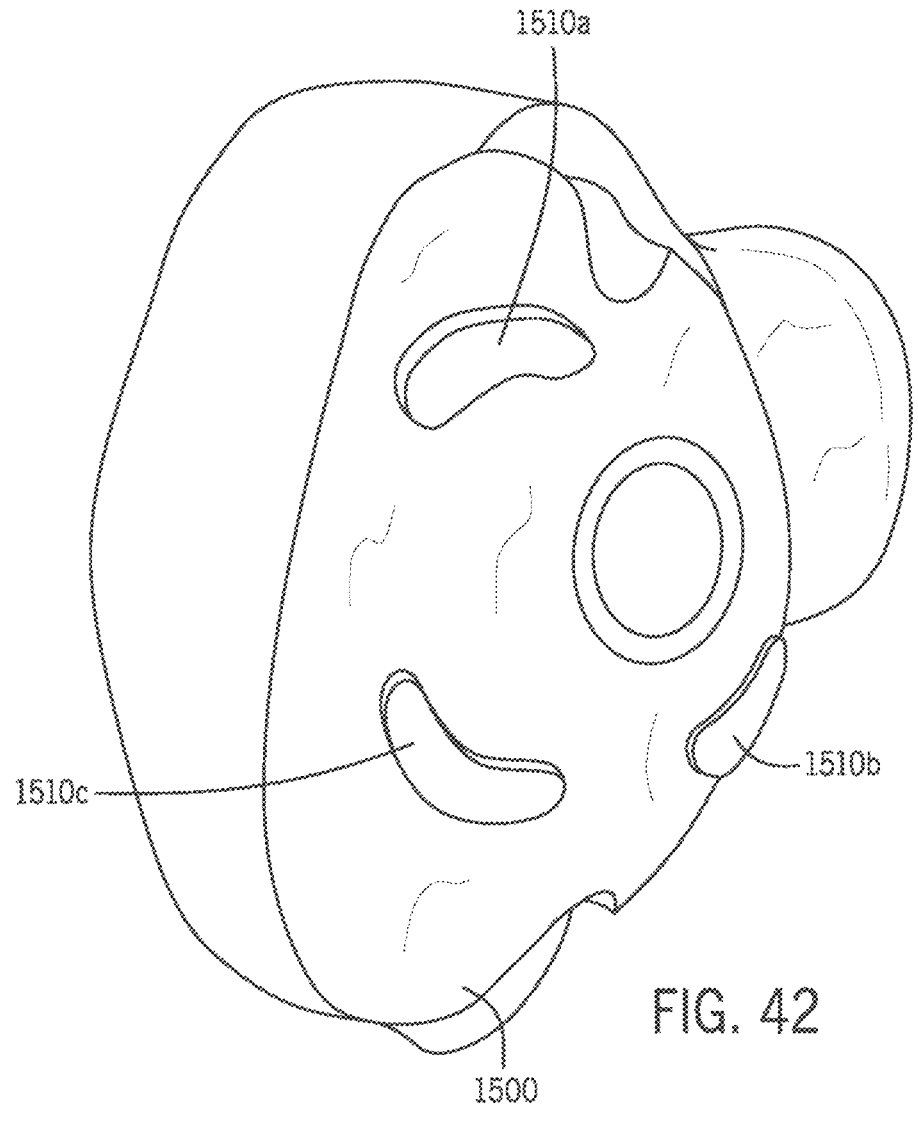
FIG. 42 is a perspective view of a glenoid baseplate according to another implementation that is configured for engaging with the physical scapula model shown in FIG. 41.

In another implementation shown in FIG. 42, the glenoid component 1500 is manufactured with a first protrusion 1510a, second protrusion 1510b, and third protrusion 1510c. The protrusions 1510a, 1510b, 1510c extend from a portion of the patient specific bone contacting surface of the glenoid component 1500 and are disposed inwardly and spaced apart from the peripheral edge of the proximal section of the glenoid component 1500. The protrusions 1510a, 1510b, 1510c have the same length and are circumferentially spaced apart from each other (e.g., evenly spaced as measured from a center of each protrusion). Each protrusion 1510a, 1510b, 1510c, is configured to engage the recesses 4110a, 4110b, 4110c defined in the bone 4100 shown in FIG. 41. Thus, the glenoid component 1500 shown in FIG. 42 is configured to engage the bone 4100 shown in FIG. 41.

Figure 44:
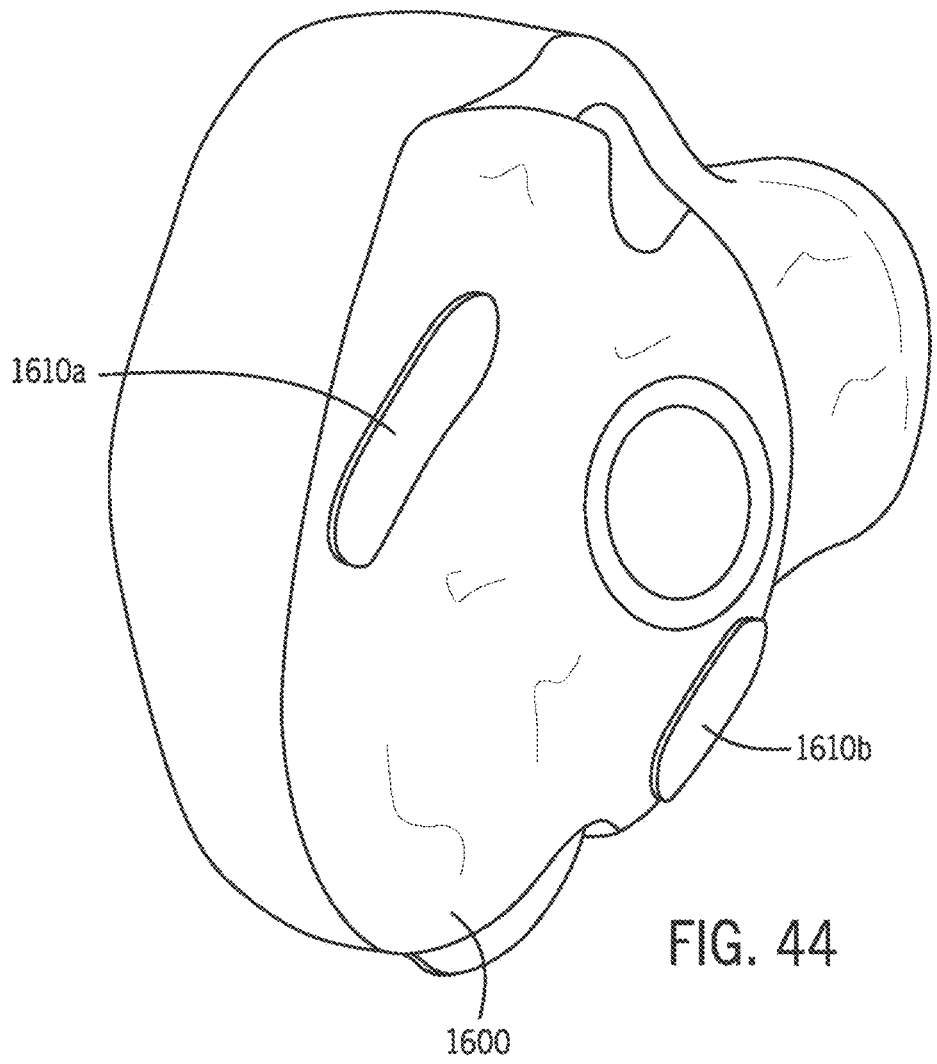
FIG. 44 is a perspective view of a glenoid baseplate according to another implementation that is configured for engaging with the physical scapula model shown in FIG. 43.

In another implementation shown in FIG. 44, the glenoid component 1600 is manufactured with a first protrusion 1610a and a second protrusion 1610b. The protrusions 1610a, 1610b extend from a portion of the patient specific bone contacting surface of the glenoid component 1600 and are disposed inwardly and spaced apart from the peripheral edge of the proximal section of the glenoid component 1600. The protrusions 1610a, 1610b have the same length and are diametrically opposed and spaced apart from each other. The protrusions 1610a, 1610b are configured for engaging the recesses 4310a, 4310b of the bone 4300 shown in FIG. 43. Thus, the glenoid component 1600 shown in FIG. 44 is configured to engage the bone 4300 shown in FIG. 43.

Figure 46:
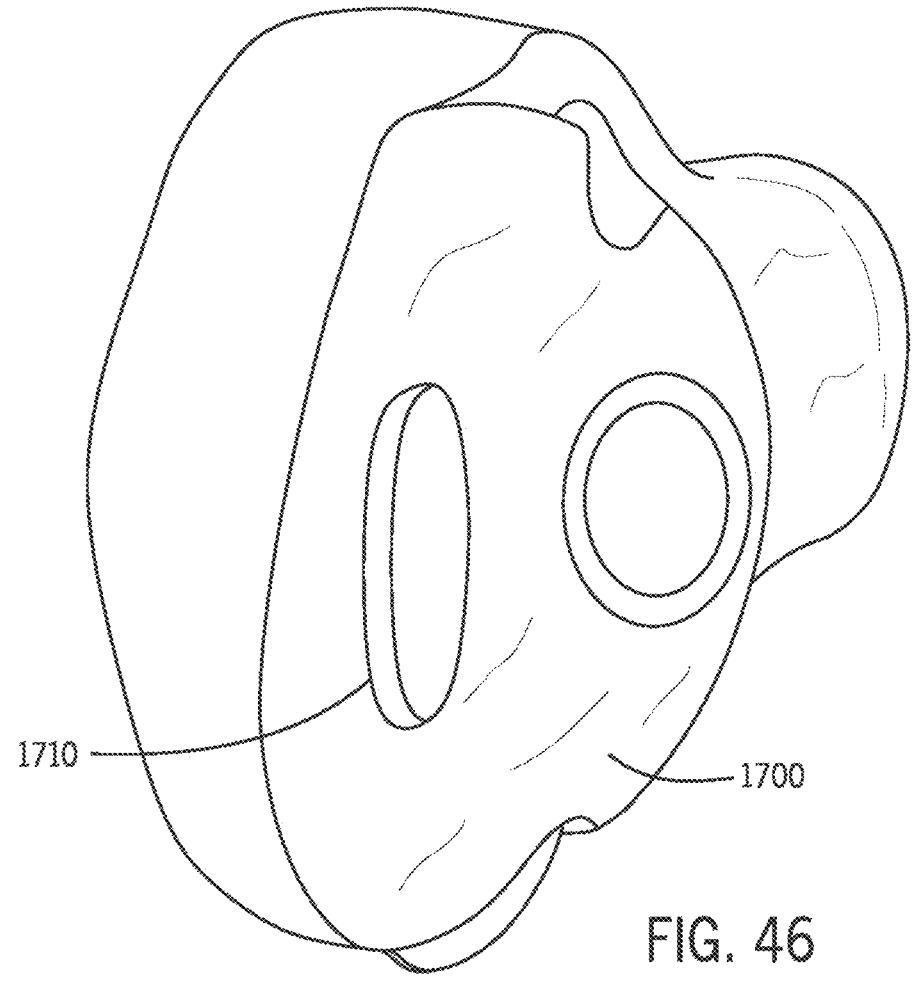
FIG. 46 is a perspective view of a glenoid baseplate according to another implementation that is configured for engaging with the physical scapula model shown in FIG. 45.

In another implementation shown in FIG. 46, the glenoid component 1700 is manufactured with a protrusion 1710. The protrusion 1710 extends from a portion of the patient specific bone contacting surface of the glenoid component 1700 and is disposed inwardly and spaced apart from the peripheral edge of the proximal section of the glenoid component 1700. The protrusion 1710 is also spaced apart from a center of the component 1700. The protrusion is configured to engage the recess 4510 defined in bone 4500 shown in FIG. 45. Thus, the glenoid component 1700 shown in FIG. 46 is configured to engage the bone 4500 shown in FIG. 45.

In other implementations, the protrusions may have the same length or different lengths. Also, in other implementations, the protrusions may have a length that varies along the distal contour surface of the respective protrusion.

In addition, in other implementations, the implant component may include any combination of protrusions described and shown herein. For example, the implant component may include one or more protrusions defined inwardly and spaced apart from a peripheral edge of patient specific bone contacting surface of the implant component and/or one or more protrusions defined along or directly adjacent to at least a portion of the peripheral edge of the patient specific bone contacting surface.

The insertion instrument 1000 is positioned on the glenoid component 1100 with the component contacting surface 1016 of the insertion instrument 1000 contacting the first surface 1120 of the glenoid component 1100 for ensuring a custom fit of the glenoid component contacting surface 1016 and the first proximal surface 1120 of the glenoid component 1100. These surfaces 1016, 1120 are 3D printed to match in shape ensuring that the glenoid component 1100 can be placed on the insertion instrument 1000 in only one correct orientation. The insertion instrument 1000 is then positioned such that the coracoid pin 116 is located in the locating pin hole 1002 and the glenoid pin 114 is located in the additional locating pin hole 1004 after passing through the inset 1104 of the glenoid component 1100. The insertion instrument 1000 is moved towards the scapula 71, and the protrusion 1177 of the glenoid component 1100 fits exactly into any of bone preparations 910a, 910b, 910c, 910d, 910e in the scapula 71. The insertion instrument 1000 and the glenoid component 1100 facilitate accurate placement and increase implant stability. The glenoid component 1200 may be placed in the scapula 71 in the same manner. Although the insertion instrument 1000 is described as positioned on the glenoid component 1100 shown in FIG. 20, the insertion instrument is also able to be positioned with other components, such as glenoid components 1200, 1300, 1400, 1500, 1600, 1700 described herein.

Figure 22:
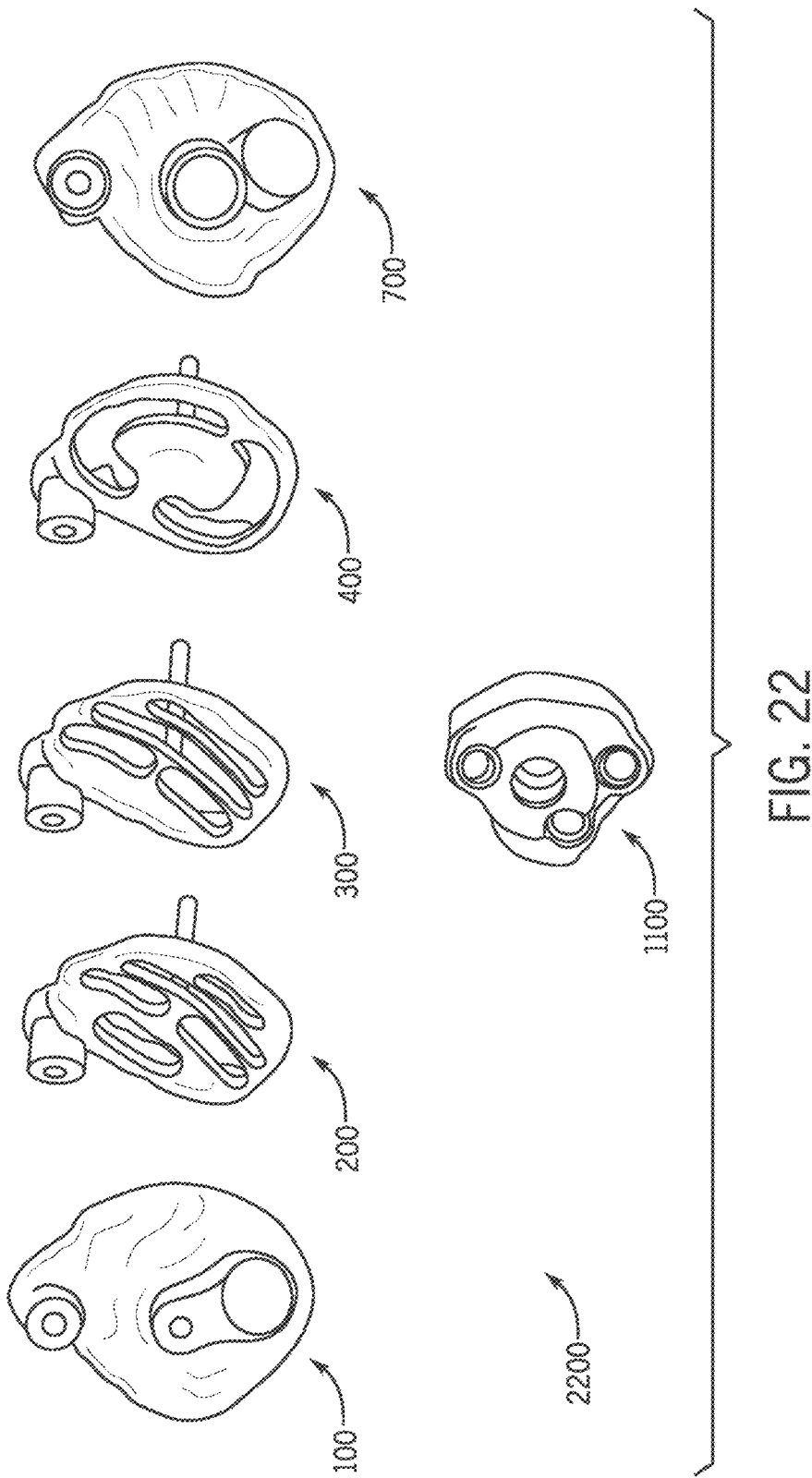
FIG. 22 is a top view of a kit for use in implanting a component of an implant in a bone of a patient according to one example implementation of the present disclosure.

FIG. 22 shows a non-limiting example kit 2200 for practicing the methods disclosed herein. Each of the locating pin guide 100, the first cutting tool template 200, the second cutting tool template 300, the third cutting tool template 400, the fourth cutting tool template 700, and the glenoid component 1100 can be fabricated using 3D printing based on a three-dimensional model of the scapula 71 of the patient reconstructed from image scans of the scapula of the patient as described above.

Although the implementations above describe fabricating using 3D printing, other suitable systems and methods of fabrication may be used, such as casting.

Overview of an Implementation of the Method

Step 1: Through the custom pin guide, place two parallel pins: one on the glenoid surface and the second in the base of the coracoid. This will control the preparation and placement in all three planes. Next, remove the pin on the glenoid surface but leave the pin in the coracoid in place.

Step 2: Cutting templates are used with a burr that has a consistent depth and width of bone removal. The templates can be made out of metal, plastic, or any material. In one iteration, three templates are used resulting in a consistent depth of bone removal across the irregularly shaped glenoid surface. However, one can decide how many templates are desired based on an individual patient and size of the custom implant to be used. Place the first cutting template over the glenoid such that it is guided by the coracoid Steinman pin. Each of the guides has a post on the backside allowing the guide to fit securely in the hole drilled in the glenoid surface. Together with the pin through the coracoid, this ensures the correct rotational and depth of the bone removal. The burr has a collar that prevents contact of the metal burr against the guide. Repeat step using a second cutting template and a third cutting template. There is slight overhang of the channels created by the guides ensuring that the surface is uniform with complete bone removal.

Step 3: A cannulated reamer is used to a set the depth to remove bone at the central pin location and create an inset for the implant facilitating stability and correct seating.

Step 4: Attach the insertion instrument into the implant by placing the post with a stabilizer (e.g., O-ring) into the implant. Fully connect the insertion instrument and implant by aligning the proximal side of the implant to the recessed contours of the insertion instrument. When the implant is fully seated against the insertion instrument, there should be a minimal gap present between the insertion instrument and the implant since the insertion instrument is manufactured to match the contours of the surface of the implant. The implant is manufactured with a protrusion having a length measured proximally to distally that matches the depth of bone removal. This facilitates bone ingrowth, accurate placement, as well as implant stability. The inserter additionally acts as a drill guide for the screws.

Overview of Another Implementation of the Method

FIG. 35 is a flow chart of another method 3500 according to one example implementation of the present disclosure for implanting a component of an implant in a bone of a patient. In step 3510, a three-dimensional model of the bone of the patient is created by reconstructing image scans of the bone of the patient. Digital patient-specific image information can be provided by any suitable means known in the art, such as a computer tomography (CT) scanner, a magnetic resonance imaging (MRI) scanner, or a combination thereof. For example, the step may comprise the steps of obtaining 2D datasets of the bone of the patient and reconstructing a 3D virtual bone model from the 2D datasets. The output of the bone scan can be a stack of two-dimensional (2D) slices forming a 3D data set. The output of the scan can be digitally imported into a computer program and may be converted using algorithms known in the field of medical image processing technology to produce a 3D computer model of the relevant bone of the patient.

In step 3520, a three-dimensional model of a component to be implanted in the bone is created. In one implementation, the bone can be a scapula, and the component can be a glenoid baseplate. In one implementation, the component includes a protrusion having a length corresponding to a depth of a bone preparation in the bone.

In step 3530, the three-dimensional model of the bone is modified to include a virtual bone preparation in the three-dimensional model of the bone, wherein the virtual bone preparation is dimensioned to ensure a custom fit of the three-dimensional model of the component in the virtual bone preparation in the modified three-dimensional model of the bone. The three-dimensional model of the bone can be modified using algorithms known in the field of medical image processing technology to produce a modified 3D computer model having the virtual bone preparation.

In step 3540, the component is fabricated based on the three-dimensional model of the component. The component can be fabricated using 3D printing based on the three-dimensional model of the component.

In step 3550, surface portions of the bone are removed using a robotic device following an operating sequence based on the virtual bone preparation in the modified three-dimensional model of the bone thereby creating a bone preparation in the bone, wherein the bone preparation is dimensioned to ensure a custom fit of the component in the bone preparation in the bone. The robotic device can be a bone mounted robotic-assisted surgery system, a free standing robotic-assisted surgery system, or a bed-mounted robotic-assisted surgery system. The robotic device can be located with respect to the bone of the patient by registering the robotic device to the actual patient's bone using imaging data. The registration process can provide the robotic device's position and orientation in three-dimensional space along (x, y, z) axes relative to the patient's position, orientation and/or anatomical axes.

In step 3550, the bone preparation can be created using a cutting tool of the robotic device. A cutting path of the cutting tool can create the bone preparation in the bone, and the cutting path can be based on the virtual bone preparation in the modified three-dimensional model of the bone. The cutting path of the cutting tool creates the bone preparation in the bone such that a uniform depth of the surface of the bone is removed.

In step 3550, the robotic device can comprise a cutting tool position locator and a motion controller in communication with the cutting tool position locator. The motion controller can include a computer processor that is configured to execute computer readable instructions stored in a memory in communication with the processor. Execution of the instructions causes the robotic device to move a cutting tool (e.g., via an actuator) in the cutting path based on signals received by the motion controller from a locating marker. In one implementation, the locating marker is positioned on the patient. In one implementation, the robotic device positions a locating marker on the patient based on the three-dimensional model of the bone. In one implementation, the robotic device comprises a cutting tool, the cutting tool position locator, and the motion controller in communication with the cutting tool position locator and the cutting tool. Execution of the instructions causes the robotic device to: (i) receive signals from the locating marker, and (ii) move the cutting tool in a cutting path that creates the bone preparation in the bone, wherein the cutting path is based on the virtual bone preparation in the modified three-dimensional model of the bone. In one implementation, the robotic device positions the locating marker on the patient by (i) positioning a locating marker guide on the bone such that a patient specific bone contacting surface of the locating marker guide matingly engages a predetermined surface region on the bone, and (ii) inserting the locating marker through a throughhole of the locating marker guide.

In some implementations, the cutting tool position locator may be a camera or other suitable sensor to detect light or a signal from the locating marker, and the locating marker may be an RFID tag, a pin or screw, a stylet, or a laser or other light source directed to the relevant portion of the bone.

In one implementation, the robotic device positions a cutting template on the bone of the patient based on the three-dimensional model of the bone, and the robotic device comprises a cutting tool, a cutting tool position locator, and a motion controller in communication with the cutting tool position locator. The motion controller includes a computer processor that can be configured to execute computer readable instructions stored in a memory in communication with the processor. The instructions cause the robotic device to: (i) receive signals from a locating marker, and (ii) move the cutting tool in one or more cutting guide slots of the cutting template to create the bone preparation in the bone. In one implementation, the cutting template includes a patient specific bone contacting surface configured to contact the bone for ensuring a custom fit of the cutting tool template and a predetermined region on the bone. The locating marker can be positioned on the patient.

Overview of Another Implementation of the Method

FIG. 36 is a flow chart of another method 3600 according to one example implementation of the present disclosure for implanting a component of an implant in a bone of a patient. In step 3610, a three-dimensional model of the bone of the patient is created by reconstructing image scans of the bone of the patient. Digital patient-specific image information can be provided by any suitable means known in the art, such as a computer tomography (CT) scanner, a magnetic resonance imaging (MRI) scanner, or a combination thereof. For example, the step may comprise the steps of obtaining 2D datasets of the bone of the patient and reconstructing a 3D virtual bone model from the 2D datasets. The output of the bone scan can be a stack of two-dimensional (2D) slices forming a 3D data set. The output of the scan can be digitally imported into a computer program and may be converted using algorithms known in the field of medical image processing technology to produce a 3D computer model of the relevant bone of the patient.

In step 3620, a three-dimensional model of a component to be implanted in the bone is created. In one implementation, the bone can be a scapula, and the component can be a glenoid baseplate. In one implementation, the component includes a protrusion having a length corresponding to a depth of a bone preparation in the bone.

In step 3630, the three-dimensional model of the bone is modified to include a virtual bone preparation in the three-dimensional model of the bone, wherein the virtual bone preparation is dimensioned to ensure a custom fit of the three-dimensional model of the component in the virtual bone preparation in the modified three-dimensional model of the bone. The three-dimensional model of the bone can be modified using algorithms known in the field of medical image processing technology to produce a modified 3D computer model having the virtual bone preparation.

In step 3640, the component is fabricated based on the three-dimensional model of the component. The component can be fabricated using 3D printing based on the three-dimensional model of the component.

In step 3650, the modified three-dimensional model of the bone is displayed on a mixed reality visualization device viewable by a surgeon. As used herein, the term "mixed reality" refers to the presentation of one or virtual objects (e.g., a three-dimensional model of the scapula of the patient developed during a preoperative planning phase) on a visualization device such that a user sees images that include both one or more real, physical objects (e.g., the scapula of a patient viewed during an intraoperative phase) and one or more virtual objects (e.g., the three-dimensional model of the scapula of the patient developed during the preoperative planning phase). The visualization device may be head-mounted, handheld, or otherwise viewable by a user (e.g., surgeon). In some examples, in mixed reality, see-through holographic lenses may permit the user to view real-world objects, i.e., actual objects in a real-world environment, such as real anatomy, through the holographic lenses and also concurrently view virtual objects.

In step 3660, surface portions of the bone are removed by a surgeon using a cutting tool based on the virtual bone preparation in the displayed modified three-dimensional model of the bone thereby creating a bone preparation in the bone, wherein the bone preparation is dimensioned to ensure a custom fit of the component in the bone preparation in the bone. In one implementation, the mixed reality visualization device includes see-through lenses that permit the surgeon to view real-world objects, i.e., the cutting tool and the bone being prepared, through the lenses and also concurrently view virtual objects, i.e., the virtual bone preparation. The surgeon can use the cutting tool to create the bone preparation in the bone such that a uniform depth of the surface of the bone is removed based on the virtual bone preparation in the displayed modified three-dimensional model of the bone.

In step 3650, the displayed modified three-dimensional model of the bone can be registered with the bone of the patient in a field of view presented to the surgeon by the mixed reality visualization device. In one implementation, the displayed modified three-dimensional model of the bone is registered with the bone of the patient by matching one or more virtual reference points on the displayed modified three-dimensional model of the bone with one or more physical reference points on the observed bone of the patient. Then, in step 3660, after registering the displayed modified three-dimensional model of the bone with the bone of the patient, surface portions of the bone are removed within a perimeter of the virtual bone preparation viewed on the bone of the patient. The surgeon can use the cutting tool to create the bone preparation in the bone such that a uniform depth of the surface of the bone is removed based on the virtual bone preparation in the displayed modified three-dimensional model of the bone.

In step 3670, the component is implanted in the bone preparation in the bone.

EXAMPLES

The following Examples have been presented in order to further illustrate the disclosed concepts and are not intended to limit the disclosed concepts in any way. The statements provided in the Examples are presented without being bound by theory.

Example A

Research on Custom Glenoid Components

A study of 18 patients receiving custom glenoid components showed that: (i) three patients implanted had glenoid component loosening; (ii) two patients could not be adequately seated at surgery and a custom component was abandoned; and (iii) three had post-operative instability, yielding an overall 44% complication rate.

Figure 1A:
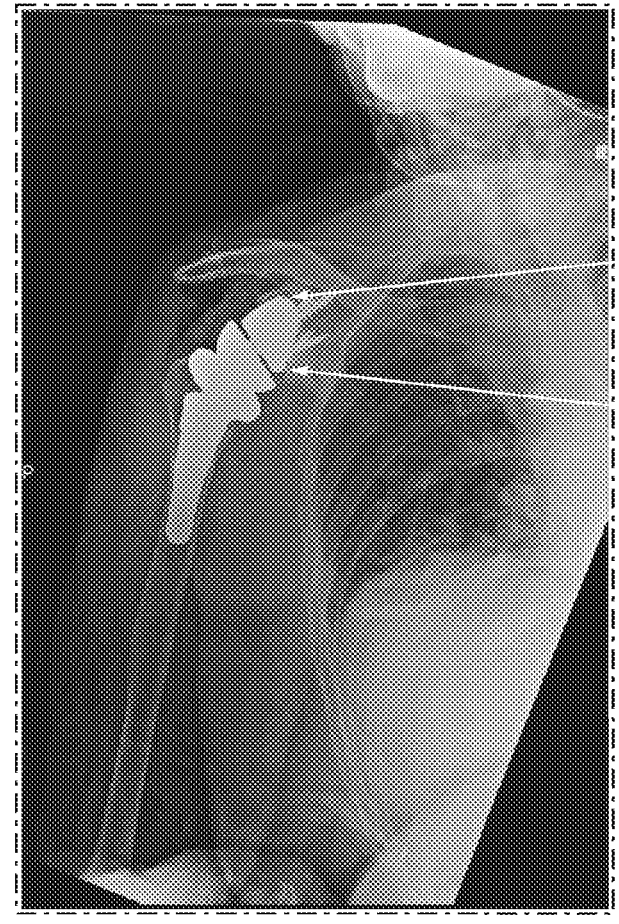
FIG. 1A is a radiograph taken immediately after surgery showing a complete gap between a custom glenoid component and underlying bone of a human patient. To get bone ingrowth into the implant, there needs to be no lucent line. Therefore, this patient is at risk of failure.
Figure 2:
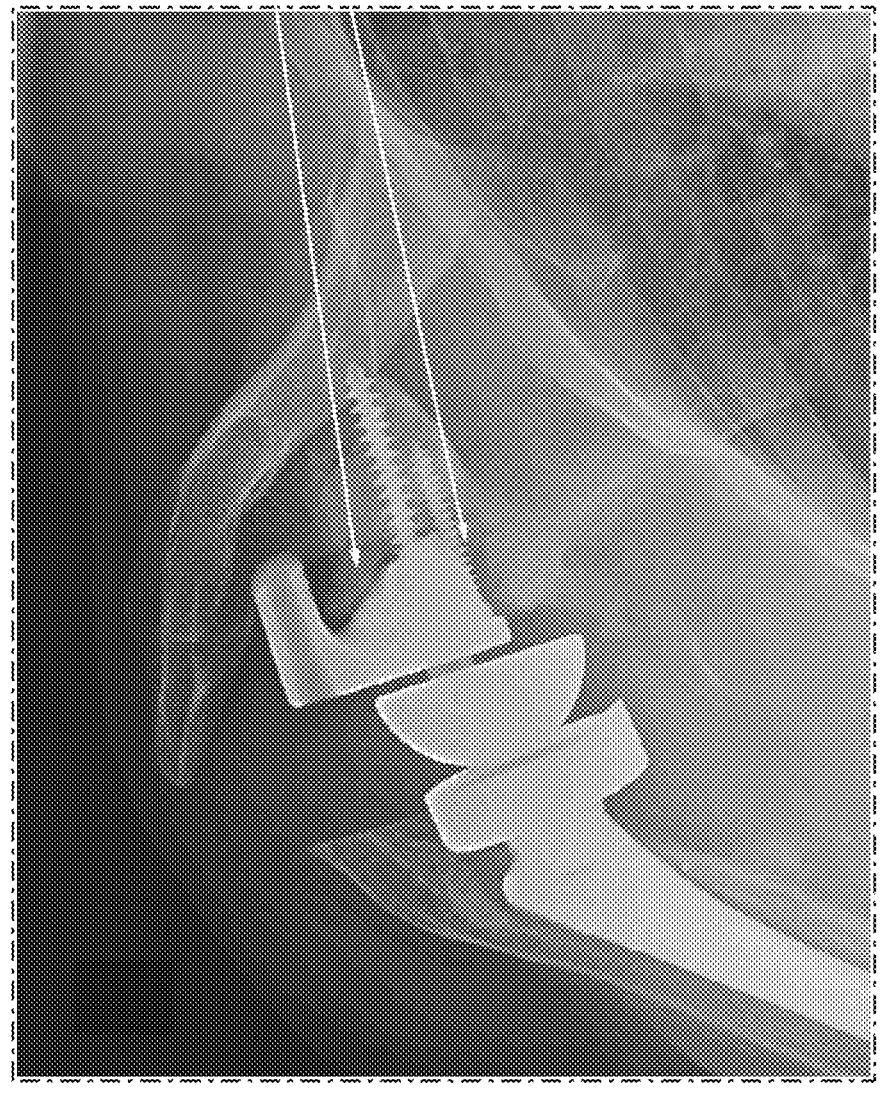
FIG. 2 is an immediate postoperative X-ray of a human patient showing a complete lucent line between a custom implant glenoid component and bone.
Figure 3:
FIG. 3 is a six-month postoperative X-ray of a human patient showing a failed custom shoulder implant with broken screws.

FIG. 1A is a radiograph taken immediately after surgery showing a complete gap between a custom glenoid component and underlying bone of a human patient. In order to get bone ingrowth into the implant, there needs to be no lucent line. Therefore, this patient is at risk of failure. FIG. 2 is an immediate postoperative X-ray of a human patient showing a complete lucent line between a custom implant glenoid component and bone. FIG. 3 is a six month postoperative X-ray of a human patient showing a failed custom shoulder implant with broken screws.

Another failed custom glenoid implant showed fibrous scar tissue with no bone ingrowth and sclerotic bone with poor ingrowth capability. See FIG. 1B.

As noted above, there is abundant research that an implant must be directly opposed to a bone surface without a gap to allow for bone ingrowth with less than a 50 micron gap. The 1000 micron (1 millimeter) gaps that are frequently present with custom implants significantly increase the chances of loosening and failure.

Example B

Verification for Reproducible Bone Preparation Using 3D Printed Models

Looking at FIGS. 23-34, a 3D printed polymeric scapula model 70A of a scapula of a patient was fabricated using 3D printing based on a three-dimensional model of the scapula of the patient reconstructed from CT image scans of the scapula of the patient.

Looking at FIG. 23, a locating pin guide 100A was fabricated using 3D printing based on the three-dimensional model of the scapula of the patient. The locating pin guide 100A included the features of the locating pin guide 100 of FIG. 5 as described above. A glenoid pin 114 was inserted through the inner throughhole of the locating pin guide 100A and into the glenoid cavity of the scapula model 70A. A coracoid pin 116 was inserted through the outer throughhole and into the base of the coracoid of the scapula model 70A. The coracoid pin 116 and the glenoid pin 114 were parallel. I chose to have the superior pin in the base of the coracoid in this Example. However, that pin could also be placed on the superior aspect of the glenoid surface or perhaps any surface.

Figure 25:
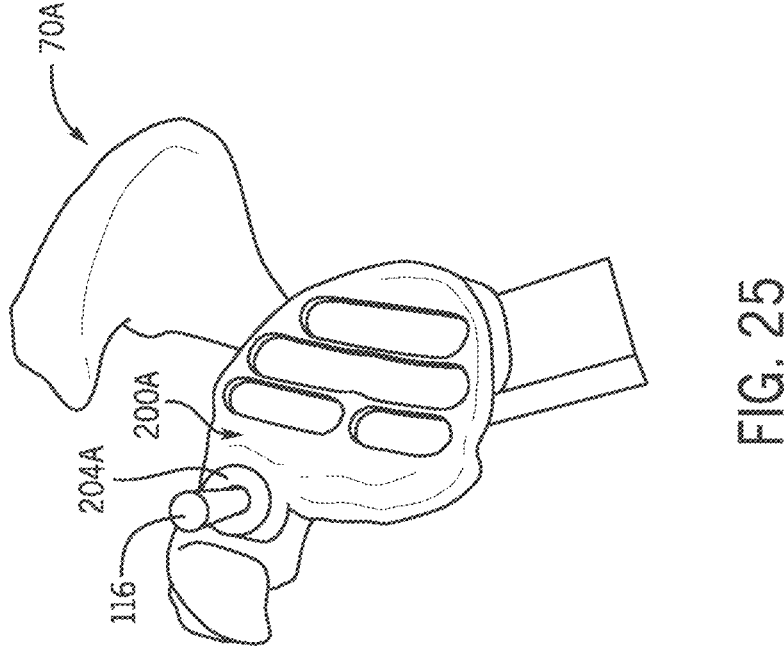
FIG. 25 is a perspective view of the first cutting tool template of FIG. 24 positioned on a scapula model.
Figure 24:
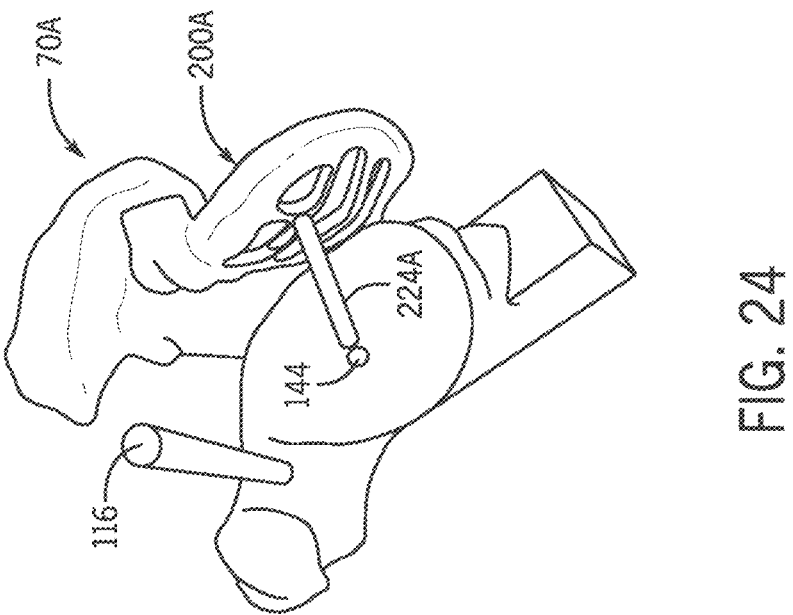
FIG. 24 is a perspective view of a first cutting tool template according to one example implementation of the present disclosure being positioned on a scapula model.
Figures 26, 27, 28:
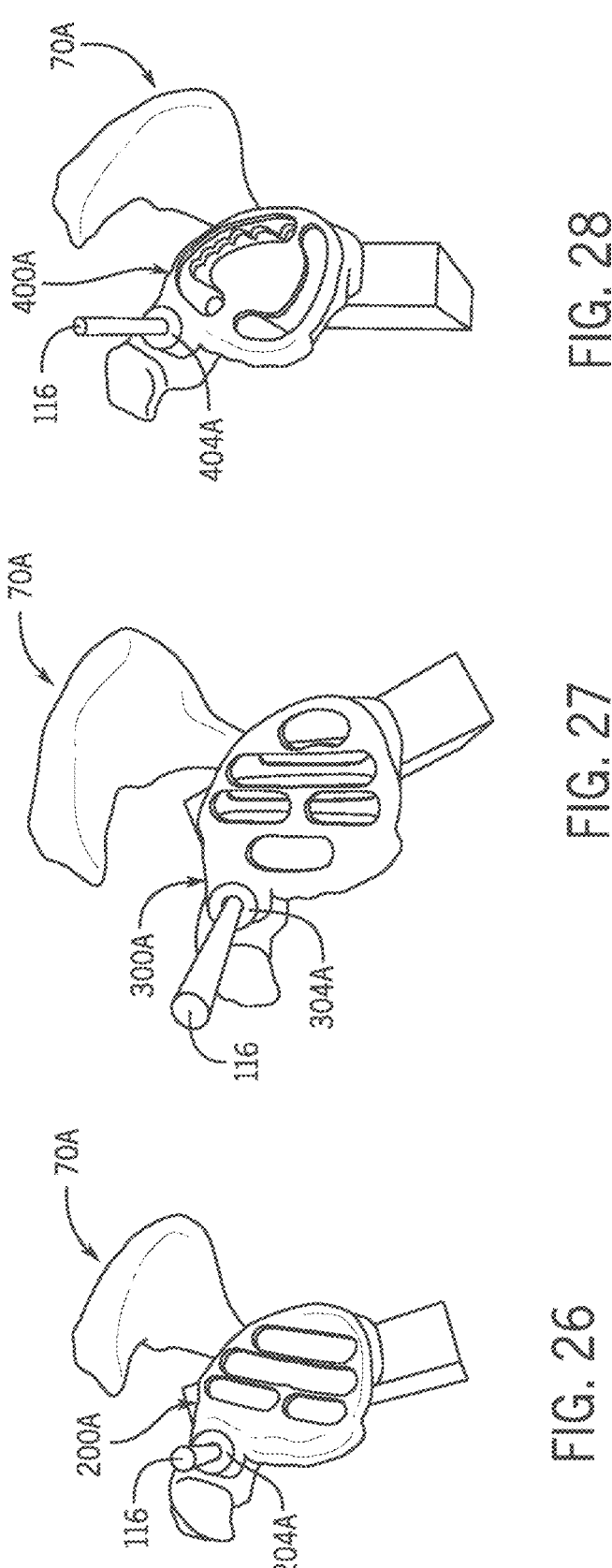
FIG. 26 is another perspective view of the first cutting tool template of FIG. 24 positioned on a scapula model.
FIG. 27 is a perspective view of a second cutting tool template according to one example implementation of the present disclosure positioned on a scapula model.
FIG. 28 is a perspective view of a third cutting tool template according to one example implementation of the present disclosure positioned on a scapula model.

Referring to FIGS. 24, 25 and 26, a first cutting tool template 200A was fabricated using 3D printing based on the three-dimensional model of the scapula of the patient. The first cutting tool template 200A included the features of the first cutting tool template 200 of FIGS. 6, 9, and 10 as described above. The coracoid pin 116 was inserted through the outer throughhole 204A, and the post 224A was inserted into hole 144. The post 224A for the central hole 144 and the pin 116 through the coracoid ensures stability and rotational control for preparation. A cutting tool was inserted into each of the plurality of cutting guide slots of the first cutting template 200A and activated to remove a portion of the surface of scapula model 70A. The first cutting tool template 200A was then removed from the scapula model 70A.

Referring to FIG. 27, a second cutting tool template 300A was fabricated using 3D printing based on the three-dimensional model of the scapula of the patient. The second cutting tool template 300A included the features of the second cutting tool template 300 of FIG. 7 as described above. The coracoid pin 116 was inserted through the outer throughhole 304A, and the post was inserted into hole 144. A cutting tool was inserted into each of the plurality of cutting guide slots of the second cutting template 300A and activated to remove a portion of the surface of scapula model 70A. The second cutting tool template 200A was then removed from the scapula model 70A.

Figure 29:
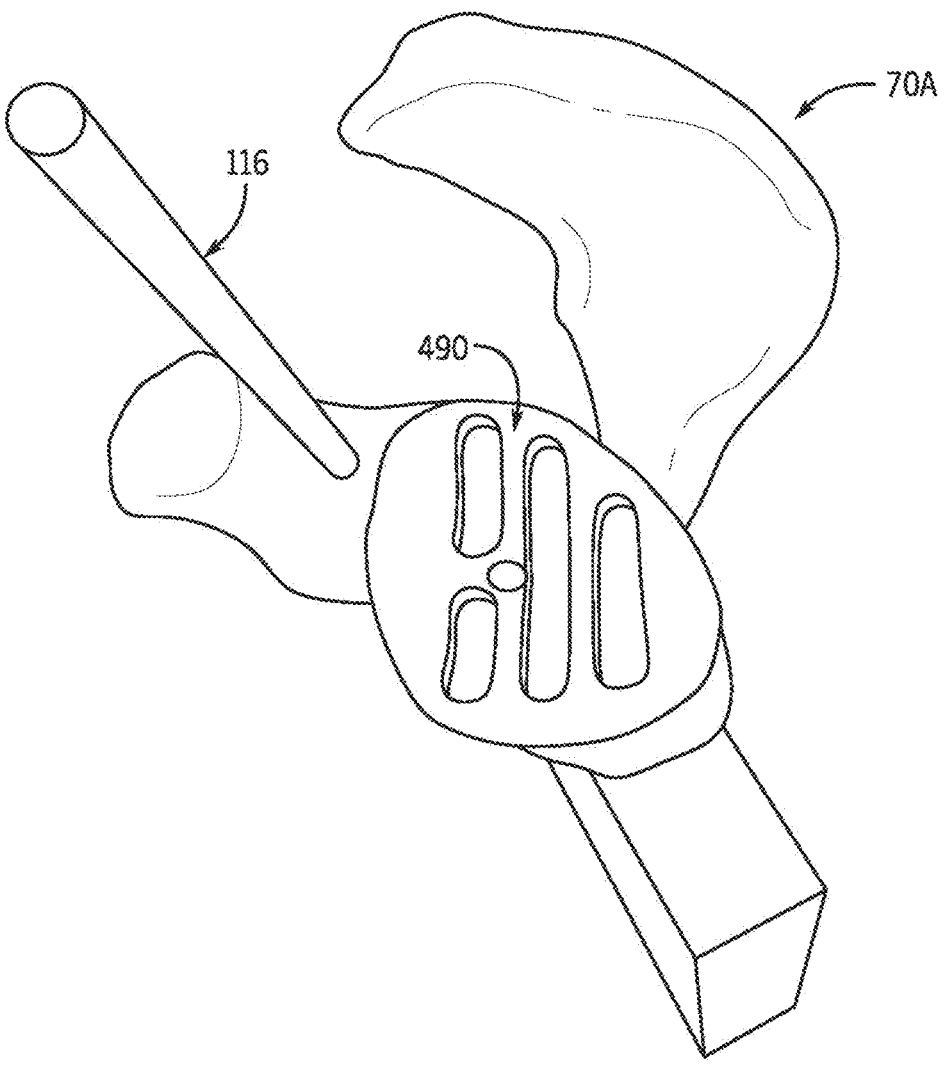
FIG. 29 is a perspective view of a partial bone preparation according to one example implementation of the present disclosure in a scapula model.

Referring to FIG. 28, a third cutting tool template 400A was fabricated using 3D printing based on the three-dimensional model of the scapula of the patient. The third cutting tool template 400A included the features of the third cutting tool template 400 of FIG. 8 as described above. The coracoid pin 116 was inserted through the outer throughhole 404A, and the post was inserted into hole 144. A cutting tool was inserted into each of the plurality of cutting guide slots of the third cutting template 400A and activated to remove a portion of the surface of scapula model 70A. The third cutting tool template 400A was then removed from the scapula model 70A. The partial bone preparation pattern 490 on the scapula model 70A is shown in FIG. 29.

Figure 30:
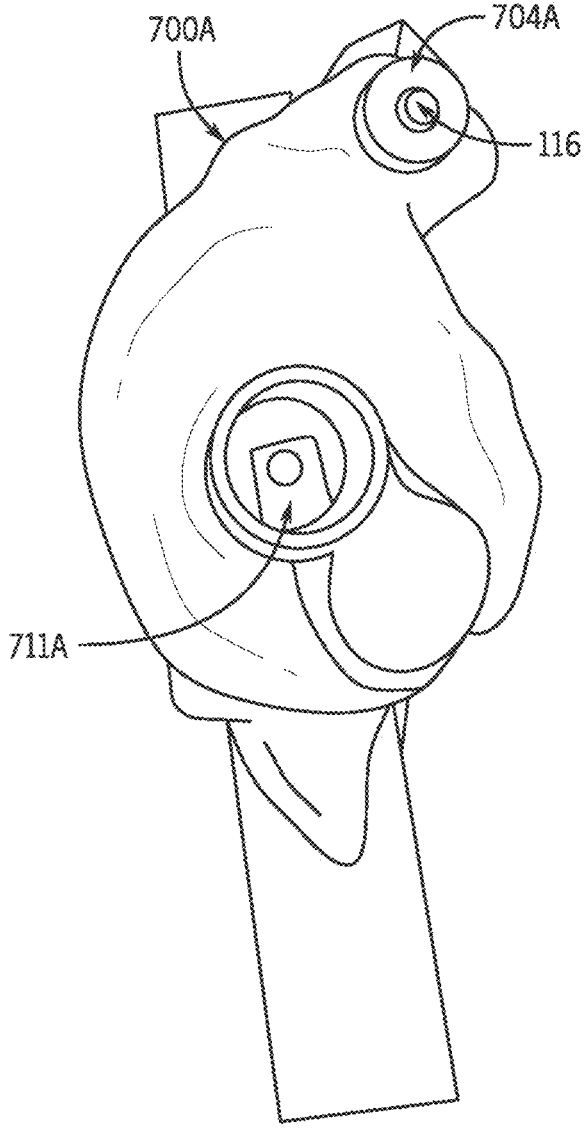
FIG. 30 is a perspective view of a fourth cutting tool template according to one example implementation of the present disclosure positioned on a scapula model.
Figure 31:
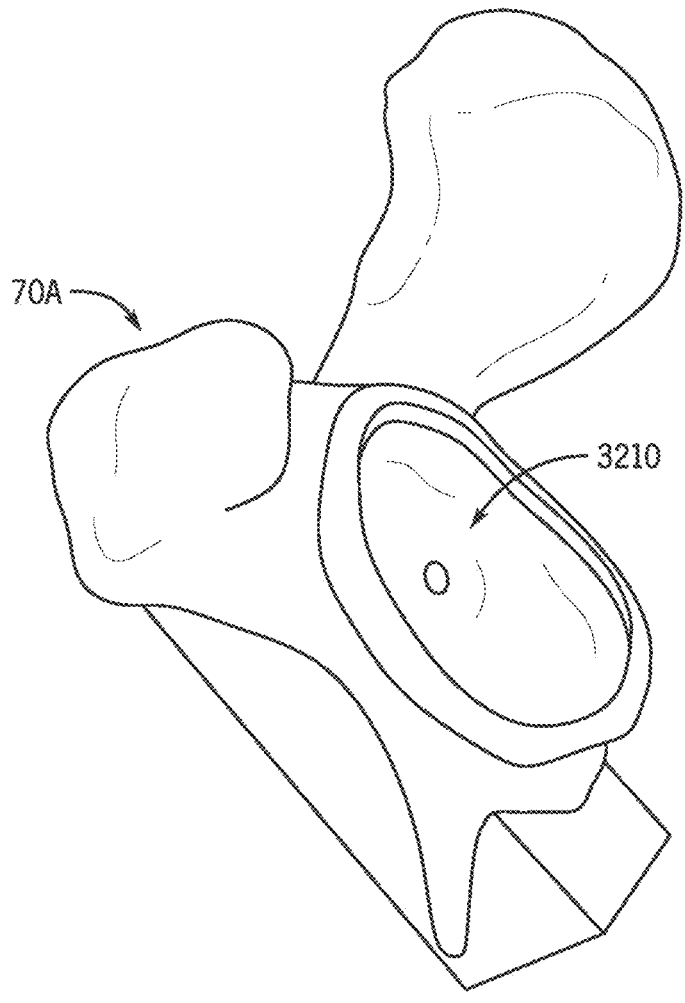
FIG. 31 is a perspective view of a bone preparation prepared according to one example implementation of the present disclosure in a scapula model.

Referring to FIG. 30, a fourth cutting tool template 700A was fabricated using 3D printing based on the three-dimensional model of the scapula of the patient. The fourth cutting tool template 700A included the features of the fourth cutting tool template 700 of FIG. 13 as described above. The coracoid pin 116 was inserted through the outer throughhole 704A. A reamer was inserted into a cutting guide aperture 711A and activated to remove a portion of the surface of scapula model 70A. The fourth cutting tool template 700A was then removed from the scapula model 70A. The bone preparation 3210 on the scapula model 70A is shown in FIGS. 31 and 32.

Figure 32:
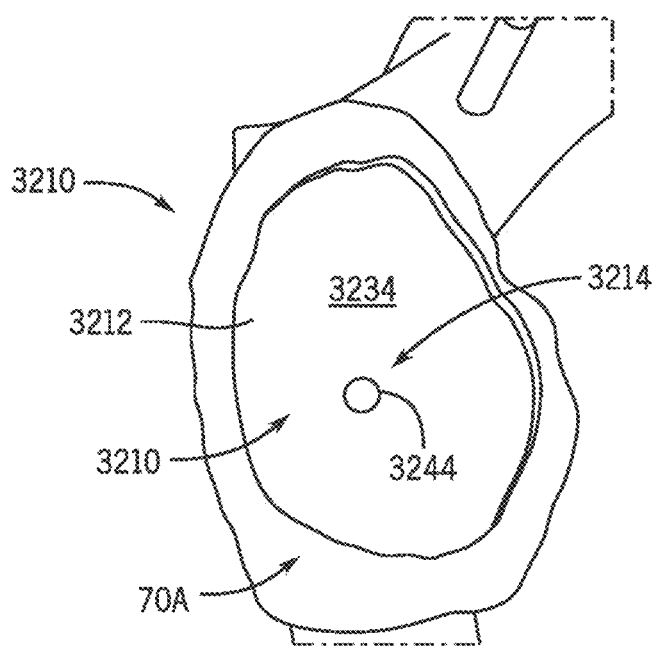
FIG. 32 is a lateral view of the bone preparation of FIG. 31 in a scapula model.

Looking at FIG. 32, the scapula model 70A included a uniform depth bone preparation 3210. The uniform depth bone preparation 3210 prepared in the scapula model 70A included a bone preparation proximal perimeter edge 3212 formed by the use of the cutting tool and the cutting templates 200A, 300A, 400A, an inner depression 3214 formed by the cannulated reamer in the inner surface 3234, and a positioning hole 3244 formed by the glenoid pin 114.

Figure 33:
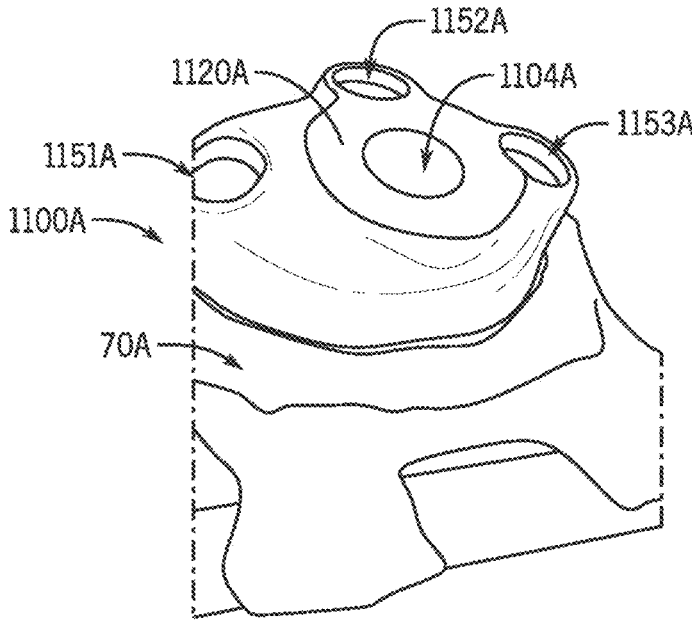
FIG. 33 is a perspective view of a glenoid baseplate according to one example implementation of the present disclosure positioned on a scapula model.
Figure 34:
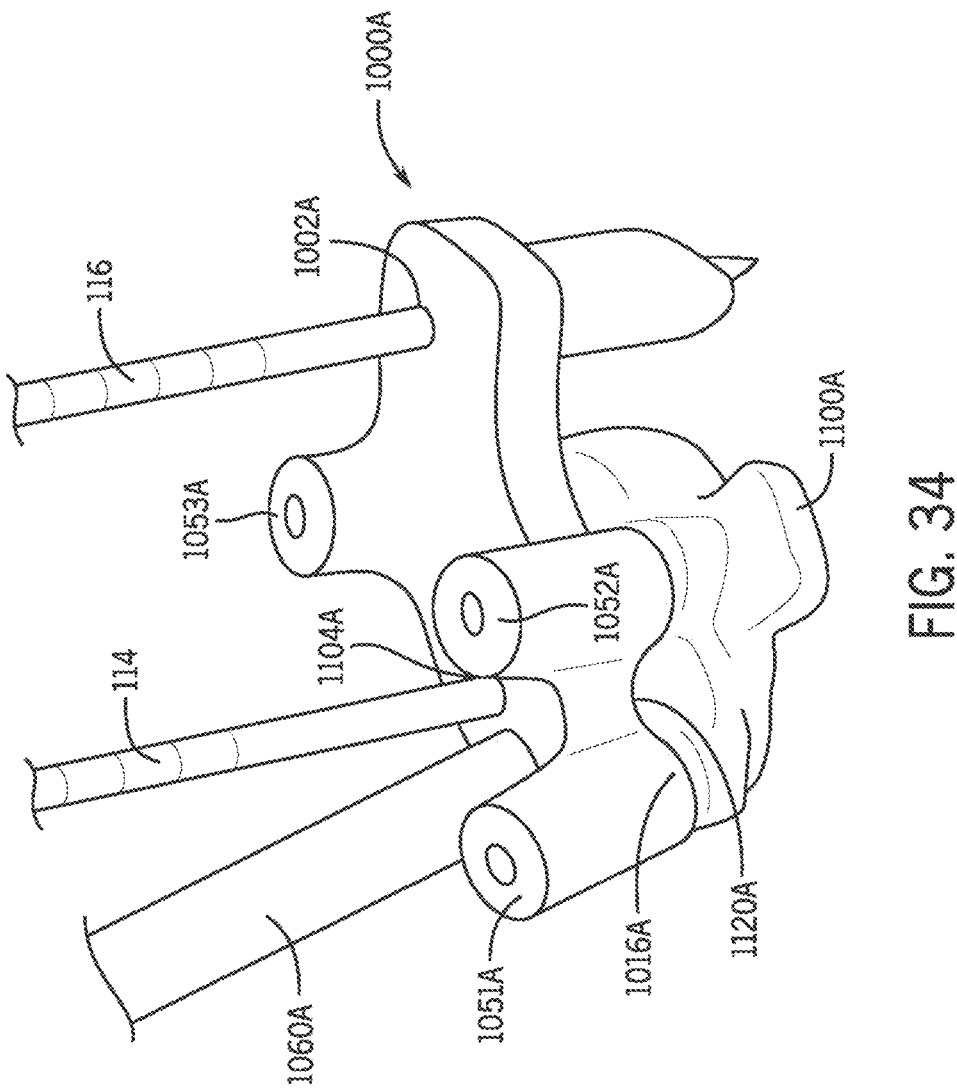
FIG. 34 is a perspective view of an insertion instrument according to one example implementation of the present disclosure positioned on a glenoid baseplate.

Looking at FIGS. 33 and 34, an insertion instrument 1000A and a glenoid component 1100A (e.g., a glenoid baseplate) were fabricated using 3D printing based on the three-dimensional model of the scapula of the patient. Looking at FIG. 34, the insertion instrument 1000A had a locating pin hole 1002A that received the coracoid pin 116, and a component contacting surface 1016A, wherein the component contacting surface 1016A was configured to contact the glenoid component 1100A for ensuring a custom fit of the glenoid component contacting surface 1016A and a first surface 1120A of the glenoid component 1100A. The insertion instrument 1000A included an additional locating pin hole 1004A dimensioned to receive the glenoid pin 114. The insertion instrument 1000A included a plurality of tubular screw guides 1051A, 1052A, 1053A radially spaced outward from the additional locating pin hole 1004A, and a handle 1060A. The glenoid component 1100A included a plurality of tubular screw receiving holes 1151A, 1152A, 1153A radially spaced outward from a tubular inset 1104A. The insertion instrument 1000A was positioned on the glenoid component 1100A with the component contacting surface 1016A contacting the first surface 1120A of the glenoid component 1100A for ensuring a custom fit of the glenoid component contacting surface 1016A and the first surface 1120A of the glenoid component 1100A. The insertion instrument 1000A was then positioned such that the coracoid pin 116 was located in the locating pin hole 1002A and the glenoid pin 114 was located in the additional locating pin hole 1004A after passing through the inset 1104A of the glenoid component 1100A. The insertion instrument 1000A was moved towards the scapula model 70A, and the glenoid component 1100A was fit exactly into the bone preparations 3210 in the scapula model 70A.

Example C

Verification for Reproducible Bone Preparation Using Cadaveric Specimen

A workflow in a cadaver with shoulder arthritis was as follows.

Pre-Operative Planning

A CT scan of the arthritic shoulder was obtained. Segmentation was completed to separate the humerus from the glenoid surface. The custom glenoid component was designed to match the patient's individual anatomy. Cutting templates were then made to ensure a consistent depth of bone removal across the irregularly shaped glenoid surface. The number of templates used was based on the size of the individual patient and custom implant to be used. There was a protrusion of metal on the custom glenoid component that corresponded in length measured proximally to distally to the depth of glenoid bone removal.

Intra-Operative Instrumentation and Component Placement

Step 1: Through the custom pin guide (see FIG. 23), two parallel pins were placed: one on the glenoid surface and the second in the base of the coracoid. This controlled the preparation and placement in all three planes. Next, the pin was removed on the glenoid surface but the pin in the coracoid was left in place.

Step 2: Cutting templates are used with a burr that had a consistent depth and width of bone removal. A first cutting template (see FIGS. 24-26) was placed over the glenoid such that it was guided by the coracoid Steinman pin. Each of the cutting templates had a post on the backside allowing the cutting template to fit securely on the glenoid surface. Together with the pin through the coracoid, this ensures the correct rotational and depth of the bone removal. The burr (see FIG. 11) had a collar that controlled depth of bone removal. The same steps were repeated using a second cutting template (see FIG. 27) and third cutting template (see FIG. 28). The channels created by the burr moving in the cutting guide slots ensured that the glenoid surface was uniform with complete bone removal.

Step 3: A cannulated reamer was used to a set the depth to remove bone at the central pin location and create an inset for the implant facilitating stability and correct seating.

Step 4: An implant Inserter was attached to the glenoid component by placing the post with an O-ring into the glenoid component. The back of the inserter matched the specific contours of the custom glenoid component ensuring that the component could only be placed in one correct orientation. The glenoid component was manufactured with a protrusion that had a length, measured proximally to distally, that matched the depth of bone removal in the glenoid. This facilitates bone ingrowth, accurate placement, as well as implant stability. The inserter additionally acted as a drill guide for the screws holding the glenoid component to the bone. A post-operative X-ray showed no gap between the bone and the glenoid component in contrast to what was seen frequently in prior glenoid component implantations.

Thus, the system disclosed herein provides for custom medical implant design and instrumentation. A patient specific, custom designed prosthesis may be built based upon image data and the methodology described above for the patient in question. In this way, the prosthetic may be created specifically for the patient using additive manufacturing, or a 3D printer capable of creating a prosthetic implant out of the required materials, such as cobalt chrome, titanium, stainless steel, or other metals, plastics, ceramics, and the like. If multiple materials are needed to build different components of a modular prosthesis, different 3D printers or other manufacturing methods may be used to make different parts that are then assembled for final implantation into the patient. A number of non-limiting examples of manufacturing techniques such as milling, molding, additive manufacturing, and others can be used as manufacturing systems that could be deployed for building the patient specific devices and instrumentation described above.

The methodology enables the ability to design patient specific asymmetric implants, such as stemless, stemmed, fracture devices, or proximal humeral replacements, where the surgeon has the ability to preoperatively determine the optimal size, shape, and orientation for a feature of an implant for a specific patient. The implant can be custom made for an individual patient with custom instrumentation to facilitate intraoperative bone preparation and implantation.

The system for custom medical implant design and instrumentation addresses key deficiencies with custom components. The instrumentation provides for precise bone preparation to create an optimal bleeding bony environment for bone ingrowth. A clearly defined area of bone preparation ensures accurate implant placement and aids in time zero implant stability. The instrumentation provides accurate means to ensure the implant is inserted in the correct orientation, and implant specific design features facilitate accurate placement and increase implant stability. Prior to this application, there was not an available means to reproducibly remove a pre-determined amount of bone from an asymmetric surface to match the asymmetric shape of the implant. In the present application, the pre-determined amount of bone removed may be uniform, which may be the most efficient and common scenario. However, it is not mandatory for the amount of bone removed to be uniform. Based on the underlying bone architecture, one could specifically plan that more bone is removed in one section compared to another.

EXEMPLARY ASPECTS

In view of the described processes and compositions, hereinbelow are described certain more particularly described aspects of the disclosure. These particularly recited aspects should not, however, be interpreted to have any limiting effect on any different claims containing different or more general teachings described herein, or that the "particular" aspects are somehow limited in some way other than the inherent meanings of the language and formulas literally used therein.

In view of the many possible aspects to which the principles of the disclosed disclosure can be applied, it should be recognized that the illustrated aspects are only preferred examples of the disclosure and should not be taken as limiting the scope of the disclosure. Rather, the scope of the disclosure is defined by the following claims. We, therefore, claim as our disclosure all that comes within the scope and spirit of these claims.

Example 1

A kit for use in implanting a component of an implant in a bone of a patient, the kit comprising: (i) a locating pin guide having an inner throughhole, an outer throughhole, and a first patient specific bone contacting surface configured to contact the bone for ensuring a custom fit of the locating pin guide and a first predetermined surface region on the bone, wherein the outer throughhole is dimensioned to receive a locating pin; (ii) a first cutting tool template having a first locating pin hole dimensioned to receive the locating pin, one or more cutting guide slots dimensioned to receive a cutting tool, and a second patient specific bone contacting surface, wherein the second patient specific bone contacting surface is configured to contact the bone for ensuring a custom fit of the first cutting tool template and a second predetermined region on the bone; (iii) a second cutting tool template having a second locating pin hole dimensioned to receive the locating pin, a cutting guide aperture dimensioned to receive a cutting tool, and a third patient specific bone contacting surface, wherein the third patient specific bone contacting surface is configured to contact the bone for ensuring a custom fit of the second cutting tool template and a third predetermined region on the bone; (iv) a component having a first surface and a fourth patient specific bone contacting surface configured to contact the bone for ensuring a custom fit of the component and a fourth predetermined surface region on the bone; and (v) an insertion instrument having a third locating pin hole dimensioned to receive the locating pin, and a component contacting surface, wherein the component contacting surface is configured to contact the component for ensuring a custom fit of the component contacting surface and the first surface of the component.

Example 2

The kit of example 1 wherein: the locating pin guide is dimensioned such that an inner surface of the outer throughhole is spaced apart from the first predetermined surface region on the bone when the first patient specific bone contacting surface matingly engages the first predetermined surface region on the bone.

Example 3

The kit of example 1 wherein: the bone is a bone of a joint.

Example 4

The kit of example 1 wherein: the bone is a scapula, and the component is a glenoid baseplate.

Example 5

The kit of example 1 wherein: the bone is a scapula, and a longitudinal axis of the inner throughhole is directed into an inner region of a glenoid cavity of the scapula when the first patient specific bone contacting surface matingly engages the first predetermined surface region on the scapula.

Example 6

The kit of example 5 wherein: a longitudinal axis of the outer throughhole is directed into a base of a coracoid of the scapula when the first patient specific bone contacting surface matingly engages the first predetermined surface region on the scapula.

Example 7

The kit of example 6 further comprising: a glenoid pin dimensioned for insertion through the inner throughhole and into the glenoid cavity, and a coracoid pin dimensioned for insertion through the outer throughhole and into the coracoid.

Example 8

The kit of example 1 wherein: the first patient specific bone contacting surface has a complementary shape to a bone surface of a three-dimensional model of the bone of the patient reconstructed from image scans of the bone of the patient.

Example 9

The kit of example 8 wherein: the locating pin guide is fabricated using 3D printing based on the three-dimensional model of the bone of the patient.

Example 10

The kit of example 1 wherein: the second patient specific bone contacting surface has a complementary shape to a bone surface of a three-dimensional model of the bone of the patient reconstructed from image scans of the bone of the patient.

Example 11

The kit of example 10 wherein: the first cutting tool template is fabricated using 3D printing based on the three-dimensional model of the bone of the patient.

Example 12

The kit of example 1 wherein: the third patient specific bone contacting surface has a complementary shape to a bone surface of a three-dimensional model of the bone of the patient reconstructed from image scans of the bone of the patient.

Example 13

The kit of example 12 wherein: the second cutting tool template is fabricated using 3D printing based on the three-dimensional model of the bone of the patient.

Example 14

The kit of example 1 wherein: the component is fabricated using 3D printing based on a three-dimensional model of the bone of the patient.

Example 15

The kit of example 1 wherein: the insertion instrument is fabricated using 3D printing based on the first surface of the component.

Example 16

The kit of example 1, wherein the component comprises at least one protrusion, the protrusion having a length corresponding to a depth of the bone preparation in the bone.

Example 17

A locating device for use in implanting a component of an implant in a bone of a patient, the locating device comprising: a locating pin guide having an inner throughhole, an outer throughhole, and a patient specific bone contacting surface configured to contact the bone for ensuring a custom fit of the locating pin guide and a predetermined surface region on the bone, wherein the custom fit of the locating pin guide and the predetermined surface region on the bone extends from a first border of the locating pin guide across an inner region of the locating pin guide to a second border of the locating pin guide.

Example 18

The locating device of example 17 wherein: the bone is a bone of a joint.

Example 19

The locating device of example 17 wherein: the bone is a scapula, and the component is a glenoid baseplate.

Example 20

The locating device of example 17 wherein the locating pin guide is dimensioned such that an inner surface of the outer throughhole is spaced apart from the predetermined surface region on the bone when the patient specific bone contacting surface matingly engages the predetermined surface region on the bone.

Example 21

The locating device of example 20 wherein: the bone is a scapula, and a longitudinal axis of the inner throughhole is directed into an inner region of a glenoid cavity of the scapula when the patient specific bone contacting surface matingly engages the predetermined surface region on the scapula.

Example 22

The locating device of example 21 wherein: a longitudinal axis of the outer throughhole is directed into a base of a coracoid of the scapula when the patient specific bone contacting surface matingly engages the predetermined surface region on the scapula.

Example 23

The locating device of example 22 further comprising: a glenoid pin dimensioned for insertion through the inner throughhole and into the glenoid cavity, and a coracoid pin dimensioned for insertion through the outer throughhole and into the coracoid.

Example 24

The locating device of example 23 wherein: the coracoid pin and the glenoid pin are parallel when the glenoid pin is inserted through the inner throughhole and into the glenoid cavity and the coracoid pin is inserted through the outer throughhole and into the coracoid.

Example 25

The locating device of example 17 wherein: the patient specific bone contacting surface has a complementary shape to a bone surface of a three-dimensional model of the bone of the patient reconstructed from image scans of the bone of the patient.

Example 26

The locating device of example 25 wherein: the locating device is fabricated using 3D printing based on the three-dimensional model of the bone of the patient.

Example 27

The locating device of example 17 further comprising: a hole-forming instrument dimensioned for insertion through the inner throughhole and into a glenoid cavity to create a positioning hole in the glenoid cavity.

Example 28

A system for preparation of a surface of a bone of a patient when implanting a component of an implant in the bone of the patient, the system comprising: a cutting tool template having a locating pin hole dimensioned to receive a locating pin, one or more cutting guide slots dimensioned to receive a cutting tool, and a patient specific bone contacting surface, wherein the patient specific bone contacting surface is configured to contact the bone for ensuring a custom fit of the cutting tool template and a predetermined region on the bone, wherein the custom fit of the cutting tool template and the predetermined surface region on the bone extends from a first border of the cutting tool template across an inner region of the cutting tool template to a second border of the cutting tool template.

Example 29

The system of example 28 wherein: the cutting tool template includes a post extending away from the patient specific bone contacting surface.

Example 30

The system of example 28 further comprising: a second cutting tool template having a second locating pin hole dimensioned to receive the locating pin, a second one or more cutting guide slots dimensioned to receive the cutting tool, and a second patient specific bone contacting surface, wherein the second patient specific bone contacting surface is configured to contact the bone for ensuring a custom fit of the second cutting tool template and the predetermined region on the bone.

Example 31

The system of example 30 wherein: the cutting tool template has a first cutting guide pattern of the one or more cutting guide slots different from a second cutting guide pattern of the second one or more cutting guide slots of the second cutting tool template.

Example 32

The system of example 30 wherein: the second cutting tool template includes a post extending away from the second patient specific bone contacting surface.

Example 33

The system of example 30 further comprising: a third cutting tool template having a third locating pin hole dimensioned to receive the locating pin, a third one or more cutting guide slots dimensioned to receive the cutting tool, and a third patient specific bone contacting surface, wherein the third patient specific bone contacting surface is configured to contact the bone for ensuring a custom fit of the third cutting tool template and the predetermined region on the bone.

Example 34

The system of example 33 wherein: the cutting tool template has a first cutting guide pattern of the one or more cutting guide slots different from a second cutting guide pattern of the second one or more cutting guide slots of the second cutting tool template, and the third cutting tool template has a third cutting guide pattern of the third one or more cutting guide slots different from the second cutting guide pattern of the second one or more cutting guide slots of the second cutting tool template.

Example 35

The system of example 33 wherein: the third cutting tool template includes a post extending away from the third patient specific bone contacting surface.

Example 36

The system of example 28 wherein: the bone is a bone of a joint.

Example 37

The system of example 28 wherein: the bone is a scapula, and the component is a glenoid baseplate.

Example 38

The system of example 28 wherein the cutting tool template is dimensioned such that an inner surface of the locating pin hole is spaced apart from the predetermined surface region on the bone when the patient specific bone contacting surface matingly engages the predetermined surface region on the bone.

Example 39

The system of example 38 wherein: the bone is a scapula, and a longitudinal axis of the locating pin hole is directed into a base of a coracoid of the scapula when the patient specific bone contacting surface matingly engages the predetermined surface region on the scapula.

Example 40

The system of example 28 wherein: the patient specific bone contacting surface has a complementary shape to a bone surface of a three-dimensional model of the bone of the patient reconstructed from image scans of the bone of the patient.

Example 41

The system of example 40 wherein: the cutting tool template is fabricated using 3D printing based on the three-dimensional model of the bone of the patient.

Example 42

The system of example 28 further comprising: a cutting tool dimensioned for insertion into each of the one or more cutting guide slots to remove a portion of the surface of the bone.

Example 43

The system of example 42 wherein: the cutting tool includes a cutting depth sleeve positioned on the cutting tool such that a distal surface of the cutting depth sleeve contacts a proximal surface of the cutting tool template to limit a cutting depth of the cutting tool in the bone.

Example 44

The system of example 42 wherein: a proximal surface of the cutting tool template is shaped such that a uniform depth of the surface of the bone is removed.

Example 45

A system for preparation of a surface of a bone of a patient when implanting a component of an implant in the bone of the patient, the system comprising: a cutting tool template having a locating pin hole dimensioned to receive a locating pin, a cutting guide aperture dimensioned to receive a cutting tool, and a patient specific bone contacting surface, wherein the patient specific bone contacting surface is configured to contact the bone for ensuring a custom fit of the cutting tool template and a predetermined region on the bone, wherein the custom fit of the cutting tool template and the predetermined surface region on the bone extends from a first border of the cutting tool template across an inner region of the cutting tool template to a second border of the cutting tool template.

Example 46

The system of example 45 further comprising: a cutting tool dimensioned for insertion into the cutting guide aperture to remove a portion of the surface of the bone.

Example 47

The system of example 46 wherein: the cutting tool includes a cutting depth sleeve positioned on the cutting tool such that a distal surface of the cutting depth sleeve contacts a proximal surface of the cutting tool template to limit a cutting depth of the cutting tool in the bone.

Example 48

The system of example 46 wherein: the cutting tool comprises a cannulated reamer.

Example 49

The system of example 48 further comprising: a guide pin for insertion into the bone, wherein the cannulated reamer is dimensioned for placement around the guide pin.

Example 50

The system of example 45 wherein: the bone is a bone of a joint.

Example 51

The system of example 45 wherein: the bone is a scapula, and the component is a glenoid baseplate.

Example 52

The system of example 45 wherein the cutting tool template is dimensioned such that an inner surface of the locating pin hole is spaced apart from the predetermined surface region on the bone when the patient specific bone contacting surface matingly engages the predetermined surface region on the bone.

Example 53

The system of example 52 wherein: the bone is a scapula, and a longitudinal axis of the locating pin hole is directed into a base of a coracoid of the scapula when the patient specific bone contacting surface matingly engages the predetermined surface region on the scapula.

Example 54

The system of example 45 wherein: the patient specific bone contacting surface has a complementary shape to a bone surface of a three-dimensional model of the bone of the patient reconstructed from image scans of the bone of the patient.

Example 55

The system of example 54 wherein: the cutting tool template is fabricated using 3D printing based on a three-dimensional model of the bone of the patient.

Example 56

A system for implanting a component of an implant in a bone of a patient, wherein the component has a first surface and a bone contacting surface configured to contact the bone for ensuring a custom fit of the component and a predetermined surface region on the bone, the system comprising: an insertion instrument having a locating pin hole dimensioned to receive a locating pin, and a component contacting surface, wherein the component contacting surface is configured to contact the component for ensuring a custom fit of the component contacting surface and the first surface of the component.

Example 57

The system of example 56 wherein the insertion instrument is dimensioned such that an inner surface of the locating pin hole is spaced apart from the predetermined surface region on the bone when the bone contacting surface of the component matingly engages the predetermined surface region on the bone

Example 58

The system of example 57 wherein: the insertion instrument includes an additional locating pin hole dimensioned to receive an additional locating pin, and a longitudinal axis of the additional locating pin hole is directed into a location of the bone spaced inward from a perimeter of the bone when the bone contacting surface of the component matingly engages the predetermined surface region on the bone.

Example 59

The system of example 58 wherein: the bone is a scapula, and the longitudinal axis of the additional locating pin hole is directed into an inner region of a glenoid cavity of the scapula when the bone contacting surface of the component matingly engages the predetermined surface region on the scapula.

Example 60

The system of example 59 wherein a longitudinal axis of the locating pin hole is directed into a base of a coracoid of the scapula when the bone contacting surface of the component matingly engages the predetermined surface region on the scapula.

Example 61

The system of example 60 further comprising: a glenoid pin dimensioned for insertion through the additional locating pin hole and into the glenoid cavity, and a coracoid pin dimensioned for insertion through the locating pin hole and into the coracoid.

Example 62

The system of example 58 wherein: the insertion instrument includes a plurality of tubular screw guides radially spaced outward from the additional locating pin hole.

Example 63

The system of example 56 wherein: the bone is a bone of a joint.

Example 64

The system of example 56 wherein: the bone is a scapula, and the component is a glenoid baseplate.

Example 65

The system of example 56 wherein: the bone contacting surface of the component has a complementary patient specific shape to a bone surface of a three-dimensional model of the bone of the patient reconstructed from image scans of the bone of the patient.

Example 66

The system of example 65 wherein: the component and the insertion instrument are fabricated using 3D printing based on the three-dimensional model of the bone of the patient.

Example 67

The system of example 56 further comprising: a stabilizer dimensioned to engage the component and the insertion instrument.

Example 68

A method for implanting a component of an implant in a bone of a patient, the method comprising: (a) creating a three-dimensional model of the bone of the patient by reconstructing image scans of the bone of the patient; (b) fabricating a locating pin guide having an outer throughhole and a first patient specific bone contacting surface configured to contact the bone for ensuring a custom fit of the locating pin guide and a first predetermined surface region on the bone, wherein the outer throughhole is dimensioned to receive a locating pin, wherein the first patient specific bone contacting surface has a complementary shape to a first bone surface of the three-dimensional model of the bone of the patient; (c) fabricating a cutting tool template having a locating pin hole dimensioned to receive the locating pin, one or more cutting guide slots dimensioned to receive a cutting tool, and a second patient specific bone contacting surface, wherein the second patient specific bone contacting surface is configured to contact the bone for ensuring a custom fit of the cutting tool template and a second predetermined region on the bone, wherein the second patient specific bone contacting surface has a complementary shape to a second bone surface of the three-dimensional model of the bone of the patient; (d) positioning the locating pin guide on the bone such that the first patient specific bone contacting surface matingly engages the first predetermined surface region on the bone; (e) inserting the locating pin through the outer throughhole and into the bone; (f) disengaging the locating pin guide from the bone; (g) positioning the cutting tool template on the bone such that the locating pin is located in the locating pin hole and the second patient specific bone contacting surface matingly engages the second predetermined surface region on the bone; (h) inserting the cutting tool into one or more of the one or more cutting guide slots such that the cutting tool removes surface portions of the bone creating a bone preparation in the bone; (i) disengaging the cutting tool and the cutting tool template from the bone; and (j) implanting the component in the bone preparation in the bone.

Example 69

The method of example 68 wherein: the bone is a bone of a joint.

Example 70

The method of example 68 wherein: the bone is a scapula, and the component is a glenoid baseplate.

Example 71

The method of example 70 wherein: a longitudinal axis of the outer throughhole is directed into a base of a coracoid of the scapula when the first patient specific bone contacting surface matingly engages the first predetermined surface region on the scapula.

Example 72

The method of example 70 wherein: the locating pin guide includes an inner throughhole dimensioned to receive a hole-forming instrument, step (e) further comprises inserting the hole-forming instrument through the inner throughhole and into the bone to form a positioning hole in the bone and removing the hole-forming instrument from the bone, the cutting tool template includes a post extending away from the second patient specific bone contacting surface, and step (g) further comprises positioning the cutting tool template on the bone such that the post is located in the positioning hole.

Example 73

The method of example 72 wherein: the bone is a scapula, the component is a glenoid baseplate, and a longitudinal axis of the outer throughhole is directed into a base of a coracoid of the scapula when the patient specific bone contacting surface matingly engages the predetermined surface region on the scapula.

Example 74

The method of example 73 wherein: the hole-forming instrument comprises a glenoid pin dimensioned for insertion through the inner throughhole and into a glenoid cavity, and the locating pin comprises a coracoid pin dimensioned for insertion through the outer throughhole and into the coracoid.

Example 75

The method of example 68 wherein: the locating pin guide and the cutting tool template are fabricated using 3D printing based on the three-dimensional model of the bone of the patient.

Example 76

The method of example 68 wherein: step (c) further comprises fabricating a second cutting tool template having a second locating pin hole dimensioned to receive the locating pin, a second one or more cutting guide slots dimensioned to receive the cutting tool, and a third patient specific bone contacting surface, wherein the third patient specific bone contacting surface is configured to contact the bone for ensuring a custom fit of the second cutting tool template and a third predetermined region on the bone, wherein the third patient specific bone contacting surface has a complementary shape to a third bone surface of the three-dimensional model of the bone of the patient, and step (i) further comprises, after disengaging the cutting tool and the cutting tool template from the bone, positioning the second cutting tool template on the bone such that the locating pin is located in the second locating pin hole and the third patient specific bone contacting surface matingly engages the third predetermined surface region on the bone, and inserting the cutting tool into one or more of the second one or more cutting guide slots such that the cutting tool removes additional surface portions of the bone creating the bone preparation in the bone.

Example 77

The method of example 68 wherein: the component has a first surface and a fourth patient specific bone contacting surface configured to contact the bone for ensuring a custom fit of the component and a fourth predetermined surface region of the bone preparation.

Example 78

The method of example 77 wherein: step (j) further comprises positioning an insertion instrument having a third locating pin hole on the component and positioning the component in the bone preparation such that the locating pin is located in the third locating pin hole.

Example 79

A method for implanting a component of an implant in a bone of a patient, the method comprising: (a) creating a three-dimensional model of the bone of the patient by reconstructing image scans of the bone of the patient; (b) creating a three-dimensional model of a component to be implanted in the bone; (c) modifying the three-dimensional model of the bone to include a virtual bone preparation in the three-dimensional model of the bone, wherein the virtual bone preparation is dimensioned to ensure a custom fit of the three-dimensional model of the component in the virtual bone preparation in the modified three-dimensional model of the bone; (d) fabricating the component based on the three-dimensional model of the component; (e) removing surface portions of the bone using a robotic device following an operating sequence based on the virtual bone preparation in the modified three-dimensional model of the bone thereby creating a bone preparation in the bone, wherein the bone preparation is dimensioned to ensure a custom fit of the component in the bone preparation in the bone; and (f) implanting the component in the bone preparation in the bone.

Example 80

The method of example 79 wherein: the bone preparation is created using a cutting tool of the robotic device.

Example 81

The method of example 80 wherein: a cutting path of the cutting tool creates the bone preparation in the bone, and the cutting path is based on the virtual bone preparation in the modified three-dimensional model of the bone.

Example 82

The method of example 81 wherein: the robotic device comprises a cutting tool position locator and a motion controller, wherein the motion controller comprises a processor configured to execute computer readable instructions, the processor being in communication with a memory and the cutting tool position locator, wherein execution of the computer readable instructions causes the robotic device to move the cutting tool in the cutting path based on signals received by the motion controller from a locating marker.

Example 83

The method of example 82 wherein: the locating marker is positioned on the patient.

Example 84

The method of example 79 wherein: the robotic device positions a locating marker on the patient based on the three-dimensional model of the bone, and the robotic device comprises a cutting tool, a cutting tool position locator, and a motion controller, wherein the motion controller comprises a processor configured to execute computer readable instructions, the processor being in communication with a memory and the cutting tool position locator, wherein execution of the computer readable instructions causes the robotic device to: (i) receive signals from the locating marker, and (ii) move the cutting tool in a cutting path that creates the bone preparation in the bone, the cutting path being based on the virtual bone preparation in the modified three-dimensional model of the bone.

Example 85

The method of example 84 wherein: the robotic device positions the locating marker on the patient by (i) positioning a locating marker guide on the bone such that a patient specific bone contacting surface of the locating marker guide matingly engages a predetermined surface region on the bone, and (ii) inserting the locating marker through a throughhole of the locating marker guide.

Example 86

The method of example 79 wherein: the robotic device positions a cutting template on the bone of the patient based on the three-dimensional model of the bone, and the robotic device comprises a cutting tool, a cutting tool position locator, and a motion controller in communication with the cutting tool position locator, the motion controller comprising a processor in communication with a memory, the processor configured to execute computer readable instructions stored in the memory, the instructions causing the robotic device to: (i) receive signals from a locating marker, and (ii) move the cutting tool in one or more cutting guide slots of the cutting template to create the bone preparation in the bone.

Example 87

The method of example 86 wherein: the cutting template includes a patient specific bone contacting surface configured to contact the bone for ensuring a custom fit of the cutting tool template and a predetermined region on the bone.

Example 88

The method of example 86 wherein: the locating marker is positioned on the patient.

Example 89

The method of example 79 wherein: the component comprises at least one protrusion, the protrusion having a length corresponding to a depth of the bone preparation in the bone.

Example 90

The method of example 79 wherein: the component is fabricated using 3D printing based on the three-dimensional model of the bone of the patient.

Example 91

A method for implanting a component of an implant in a bone of a patient, the method comprising: (a) creating a three-dimensional model of the bone of the patient by reconstructing image scans of the bone of the patient; (b) creating a three-dimensional model of a component to be implanted in the bone; (c) modifying the three-dimensional model of the bone to include a virtual bone preparation in the three-dimensional model of the bone, wherein the virtual bone preparation is dimensioned to ensure a custom fit of the three-dimensional model of the component in the virtual bone preparation in the modified three-dimensional model of the bone; (d) fabricating the component based on the three-dimensional model of the component; (e) displaying the modified three-dimensional model of the bone on a mixed reality visualization device viewable by a surgeon; (f) removing surface portions of the bone based on the virtual bone preparation in the displayed modified three-dimensional model of the bone thereby creating a bone preparation in the bone, wherein the bone preparation is dimensioned to ensure a custom fit of the component in the bone preparation in the bone; and (g) implanting the component in the bone preparation in the bone.

Example 92

The method of example 91 wherein: step (e) comprises registering the displayed modified three-dimensional model of the bone with the bone of the patient in a field of view presented to the surgeon by the mixed reality visualization device.

Example 93

The method of example 92 wherein: step (e) comprises registering the displayed modified three-dimensional model of the bone with the bone of the patient by matching one or more virtual reference points on the displayed modified three-dimensional model of the bone with one or more physical reference points on an observed bone of the patient.

Example 94

The method of example 93 wherein: step (f) comprises, after registering the displayed modified three-dimensional model of the bone with the bone of the patient, removing surface portions of the bone within a perimeter of the virtual bone preparation viewed on the bone of the patient.

Example 95

The method of example 91 wherein: the component comprises at least one protrusion, the protrusion having a length corresponding to a depth of the bone preparation in the bone.

Example 96

The method of example 91 wherein: the component is fabricated using 3D printing based on the three-dimensional model of the bone of the patient.

Example 97

A component of an implant comprising: a bone contacting surface, at least a portion of the bone contacting surface having a complementary patient specific shape to a bone surface and being configured to contact the bone surface for ensuring a custom fit of the component and the bone surface, at least one protrusion that extends proximally to distally from the bone contacting surface.

Example 98

The component of example 97, wherein the at least one protrusion is disposed inwardly and spaced apart from a peripheral edge of the bone contacting surface, the protrusion extending from the bone contacting surface.

Example 99

The component of example 97, wherein the at least one protrusion extends from a peripheral edge of the bone contacting surface.

Example 100

The component of example 97 wherein the bone is a bone of a joint.

Example 101

The component of example 97 wherein the bone is a scapula, and the component is a glenoid baseplate.

Example 102

The component of example 97 wherein: at least a portion of the bone contacting surface has a complementary patient specific shape to the bone surface of a three-dimensional model of a bone of a patient reconstructed from image scans of the bone of the patient.

Example 103

The component of example 102 wherein the component is fabricated using 3D printing based on the three-dimensional model of the bone of the patient.

In light of the principles and example implementations described and illustrated herein, it will be recognized that the example implementations can be modified in arrangement and detail without departing from such principles. Also, the foregoing discussion has focused on particular implementations, but other configurations are also contemplated. In particular, even though expressions such as "in one implementation", "in another implementation," or the like are used herein, these phrases are meant to generally reference implementation possibilities, and are not intended to limit the disclosure to particular implementation configurations. As used herein, these terms may reference the same or different implementations that are combinable into other implementations. As a rule, any implementation referenced herein is freely combinable with any one or more of the other implementations referenced herein, and any number of features of different implementations are combinable with one another, unless indicated otherwise.

Although what has been described in detail here is with reference to certain implementations, one skilled in the art will appreciate that the present concepts can be practiced by someone other than with the described implementations, which have been presented for purposes of illustration and not of limitation. Therefore, the scope of the appended claims should not be limited to the description of the implementations contained herein.

The invention claimed is:

1. A kit for use in implanting a glenoid baseplate of a shoulder implant in a bone of a patient, the kit comprising:
   a locating pin guide having an inner throughhole, an outer throughhole, and a first patient specific bone contacting surface configured to contact the bone for ensuring a custom fit of the locating pin guide and a first predetermined surface region on the bone, wherein the outer throughhole is dimensioned to receive a locating pin;
   at least one cutting tool template that defines a locating pin hole dimensioned to receive the locating pin and one or more cutting guide slots dimensioned to receive a cutting tool, and the at least one cutting tool template includes a second patient specific bone contacting surface, wherein the second patient specific bone contacting surface is configured to contact the bone for ensuring a custom fit of the cutting tool template and a second predetermined region on the bone;
   a glenoid baseplate having a first surface and a third patient specific bone contacting surface configured to contact the bone for ensuring a custom fit of the component and a third predetermined surface region on the bone; and
   an insertion instrument having a second locating pin hole dimensioned to receive the locating pin, and a component contacting surface, wherein the component contacting surface is configured to contact the glenoid baseplate for ensuring a custom fit of the component contacting surface and the first surface of the component,
   wherein the kit further comprises a second cutting tool template having a third locating pin hole dimensioned to receive the locating pin, a cutting guide aperture dimensioned to receive the cutting tool, and a fourth patient specific bone contacting surface, wherein the fourth patient specific bone contacting surface is configured to contact the bone for ensuring a custom fit of the second cutting tool template and a fourth predetermined region on the bone.

2. The kit of claim 1 wherein:
the locating pin guide is dimensioned such that an inner surface of the outer throughhole is spaced apart from the first predetermined surface region on the bone when the first patient specific bone contacting surface matingly engages the first predetermined surface region on the bone.

3. The kit of claim 1 wherein:
the bone is a bone of a joint.

4. The kit of claim 1 wherein:
the bone is a scapula.

5. The kit of claim 1 wherein:
the bone is a scapula, and
a longitudinal axis of the inner throughhole is directed into an inner region of a glenoid cavity of the scapula when the first patient specific bone contacting surface matingly engages the first predetermined surface region on the scapula.

6. The kit of claim 1 wherein:
the first patient specific bone contacting surface has a complementary shape to a bone surface of a three-dimensional model of the bone of the patient reconstructed from image scans of the bone of the patient.

7. The kit of claim 1 wherein:
the second patient specific bone contacting surface has a complementary shape to a bone surface of a three-dimensional model of the bone of the patient reconstructed from image scans of the bone of the patient.

8. The kit of claim 1 wherein:
the third patient specific bone contacting surface has a complementary shape to a bone surface of a three-dimensional model of the bone of the patient reconstructed from image scans of the bone of the patient.

9. The kit of claim 1, wherein the glenoid baseplate comprises at least one protrusion, the protrusion having a length corresponding to a depth of a bone preparation in the bone.

* * * * *